US010908149B2

(12) United States Patent
Iyer et al.

(10) Patent No.: US 10,908,149 B2
(45) Date of Patent: Feb. 2, 2021

(54) DEVICES FOR FLUID MANAGEMENT

(71) Applicant: Triad National Security, LLC, Los Alamos, NM (US)

(72) Inventors: Rashi Iyer, Los Alamos, NM (US); Pulak Nath, Los Alamos, NM (US); Jen-Huang Huang, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 136 days.

(21) Appl. No.: 15/513,945

(22) PCT Filed: Sep. 24, 2015

(86) PCT No.: PCT/US2015/052043
§ 371 (c)(1),
(2) Date: Mar. 23, 2017

(87) PCT Pub. No.: WO2016/049365
PCT Pub. Date: Mar. 31, 2016

(65) Prior Publication Data
US 2017/0291173 A1    Oct. 12, 2017

Related U.S. Application Data

(60) Provisional application No. 62/054,843, filed on Sep. 24, 2014, provisional application No. 62/160,510, (Continued)

(51) Int. Cl.
*G01N 33/50* (2006.01)
*B01L 3/00* (2006.01)
(Continued)

(52) U.S. Cl.
CPC ........ *G01N 33/5064* (2013.01); *B01L 3/5027* (2013.01); *B01L 3/50273* (2013.01);
(Continued)

(58) Field of Classification Search
CPC ....... B01L 2200/027; B01L 2300/0627; B01L 2300/123; B01L 2400/0481;
(Continued)

(56) References Cited

U.S. PATENT DOCUMENTS 5,633,162 A    5/1997   Keen
6,197,575 B1   3/2001   Griffith et al.
(Continued)

FOREIGN PATENT DOCUMENTS

WO   WO 2013/085909   6/2013
WO   WO 2013/086329   6/2013
(Continued)

OTHER PUBLICATIONS

International Search Report and Written Opinion issued for International Application No. PCT/US2015/52043 dated Jan. 21, 2016 (12 pages).
(Continued)

*Primary Examiner* — Gautam Prakash
*Assistant Examiner* — Lydia Edwards
(74) *Attorney, Agent, or Firm* — Klarquist Sparkman, LLP

(57) ABSTRACT

Disclosed herein are embodiments of devices for managing fluid transport. In particular disclosed embodiments, the devices are used to manage fluid transport in reactor systems, such as bio-assessment systems, chemical synthesis reactors, and the like. The devices disclosed herein include fluid management devices, reservoir assemblies, valving systems, pumps, and combinations thereof. The devices disclosed herein are cost-efficient and user-friendly and can be implemented in a variety of reactor systems.

14 Claims, 19 Drawing Sheets

Related U.S. Application Data filed on May 12, 2015, provisional application No. 62/212,268, filed on Aug. 31, 2015.

(51) Int. Cl.
  *C12N 5/07* (2010.01)
  *F16K 7/04* (2006.01)
  *C12N 5/071* (2010.01)

(52) U.S. Cl.
  CPC ... *B01L 3/502707* (2013.01); *B01L 3/502715* (2013.01); *B01L 3/502738* (2013.01); *C12N 5/06* (2013.01); *G01N 33/5014* (2013.01); *G01N 33/5082* (2013.01); *B01L 2200/027* (2013.01); *B01L 2300/0627* (2013.01); *B01L 2300/0681* (2013.01); *B01L 2300/0832* (2013.01); *B01L 2300/0887* (2013.01); *B01L 2300/123* (2013.01); *B01L 2400/0481* (2013.01); *B01L 2400/0633* (2013.01); *C12N 5/067* (2013.01); *F16K 7/045* (2013.01); *G01N 33/5008* (2013.01)

(58) Field of Classification Search
  CPC ....... B01L 2400/0633; B01L 3/502715; B01L 3/50273; B01L 3/502738; B01L 2300/0681; B01L 2300/0832; B01L 2300/0887; B01L 3/5027; B01L 3/502707; F16K 7/045; G01N 33/5082; G01N 33/50; G01N 33/5008; G01N 33/5014; G01N 33/5064; C12N 5/06; C12N 5/067; C12Q 1/025
  See application file for complete search history.

(56) References Cited

U.S. PATENT DOCUMENTS

| | | | |
|---|---|---|---|
| 6,900,056 B2 | 5/2005 | Lee et al. | |
| 7,745,210 B2* | 6/2010 | Martin | C12M 23/34 215/40 |
| 7,863,035 B2 | 1/2011 | Clemens et al. | |
| 8,278,419 B2 | 10/2012 | Jacobs | |
| 8,580,546 B2 | 11/2013 | Gonda et al. | |
| 2005/0051449 A1 | 3/2005 | Jeter | |
| 2005/0130292 A1 | 6/2005 | Ahn et al. | |
| 2007/0276508 A1 | 11/2007 | Fischer et al. | |
| 2010/0303687 A1 | 12/2010 | Blaga et al. | |
| 2011/0215107 A1 | 9/2011 | Lee | |
| 2012/0074062 A1 | 3/2012 | Jovanovic et al. | |
| 2012/0135452 A1 | 5/2012 | Shuler et al. | |
| 2012/0263631 A1 | 10/2012 | Masters et al. | |
| 2013/0273643 A1 | 10/2013 | Vickers et al. | |
| 2013/0309677 A1 | 11/2013 | Blackman et al. | |
| 2014/0170693 A1 | 6/2014 | Ince | |
| 2014/0356849 A1* | 12/2014 | Wikswo | B01L 3/5027 435/1.2 |
| 2015/0004077 A1 | 1/2015 | Wikswo et al. | |

FOREIGN PATENT DOCUMENTS

| | | |
|---|---|---|
| WO | WO 2013/086486 | 6/2013 |
| WO | WO 2013/086505 | 6/2013 |
| WO | WO 2013/181656 | 12/2013 |
| WO | WO 2014/081840 | 5/2014 |
| WO | WO 2014/127250 | 8/2014 |
| WO | WO 2015/006751 | 1/2015 |
| WO | WO 2015/138032 | 9/2015 |
| WO | WO 2015/138034 | 9/2015 |

OTHER PUBLICATIONS

International Search Report and Written Opinion issued for International Application No. PCT/US2015/052039 dated Dec. 22, 2015 (12 pages).

International Search Report and Written Opinion issued for International Application No. PCT/US2015/052046 dated Nov. 12, 2015 (11 pages).

Tavana et al., "Microfluidics, Lung Surfactant, and Respiratory Disorders," *LabMedicine*, 40(4): 204-209, Apr. 2009.

* cited by examiner

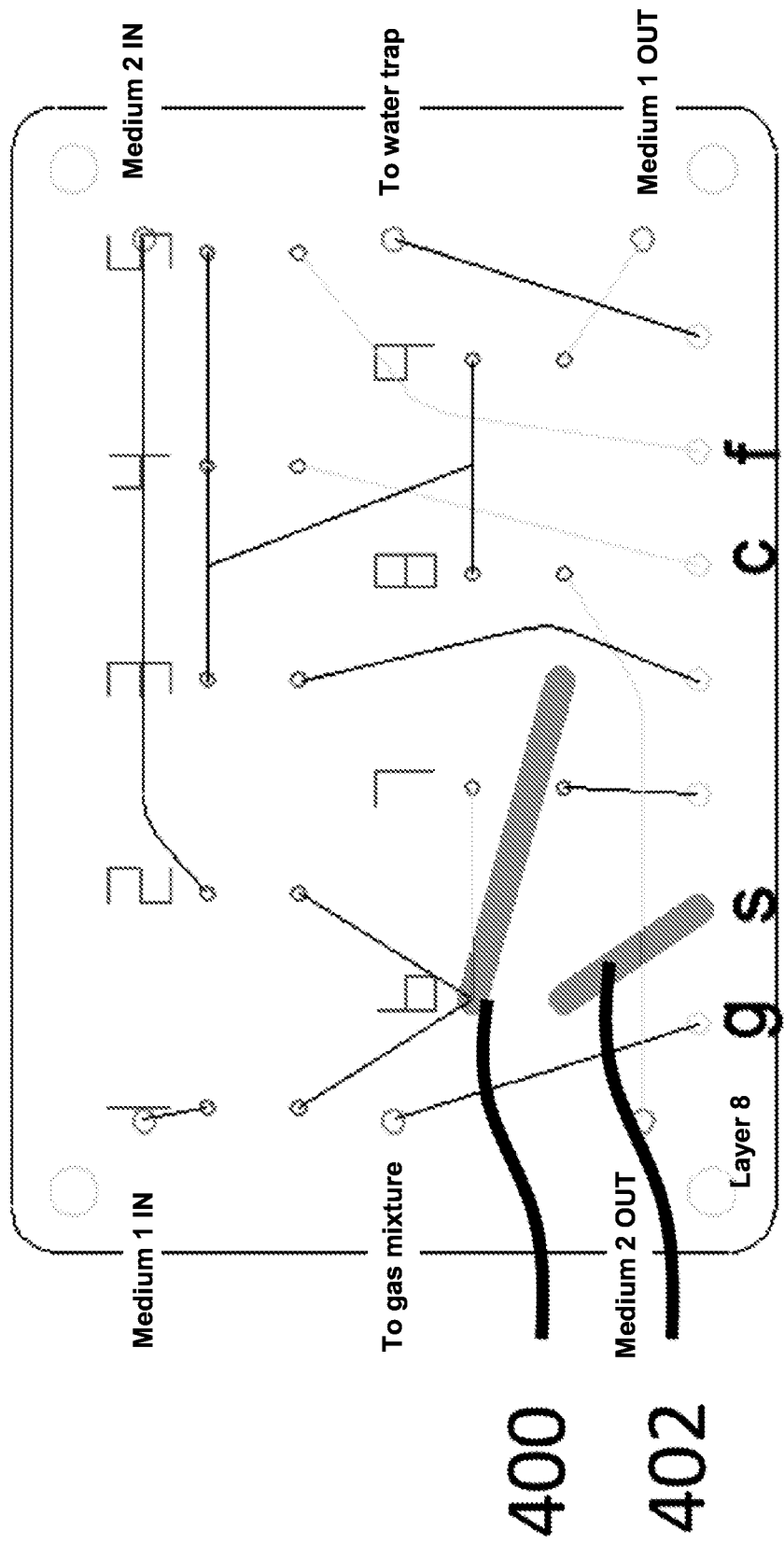

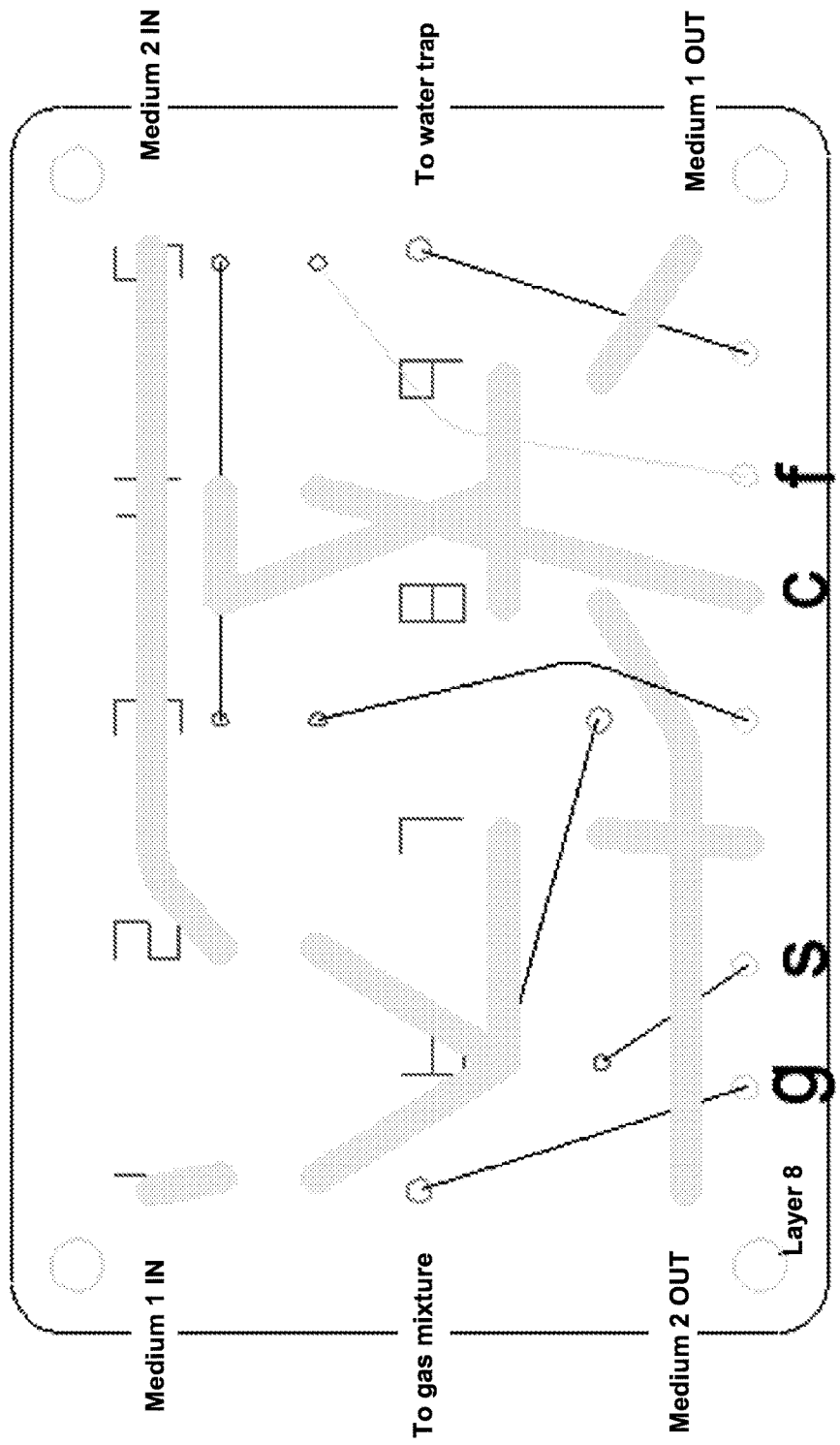

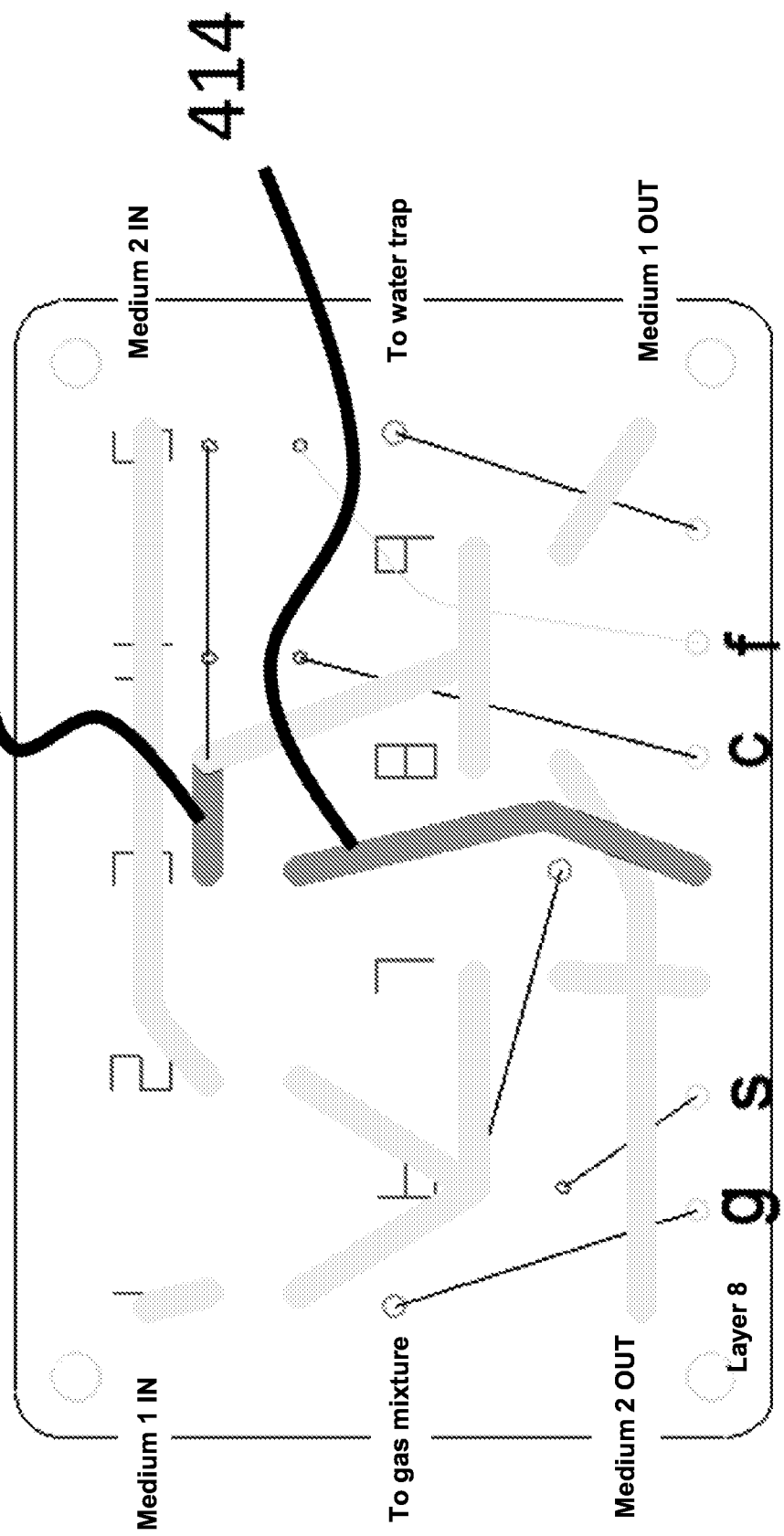

FIG. 10
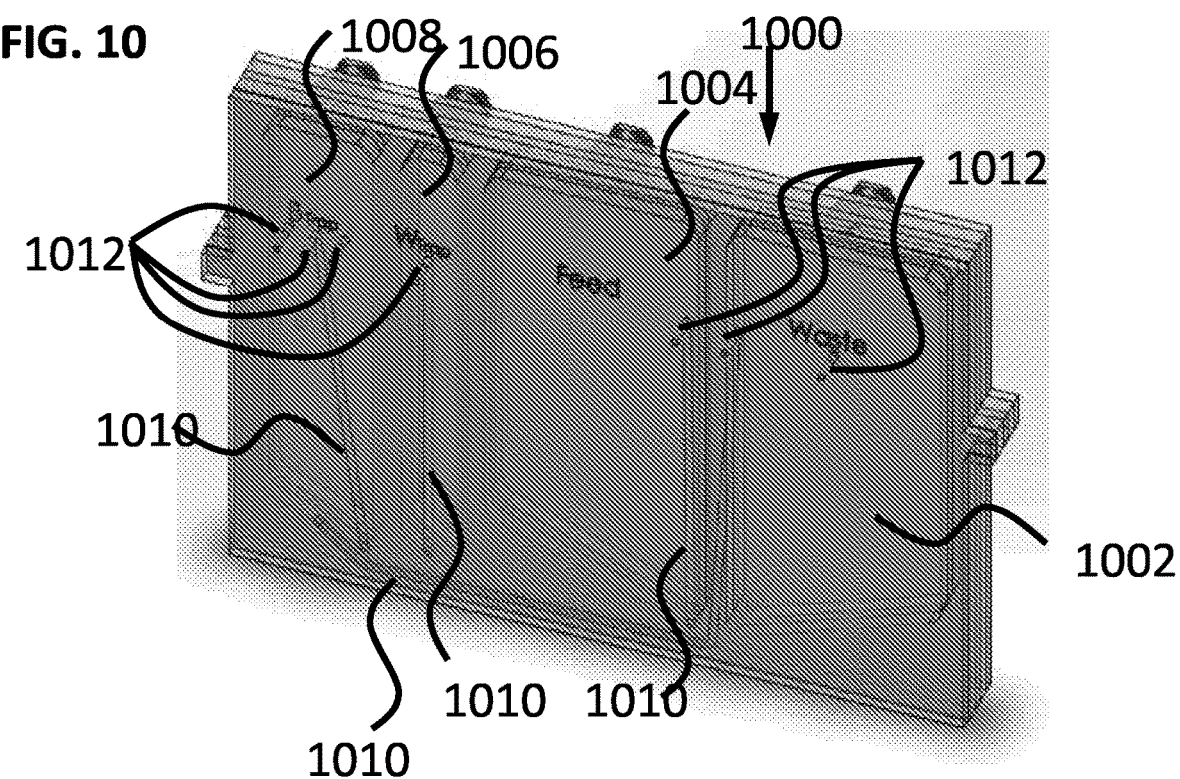
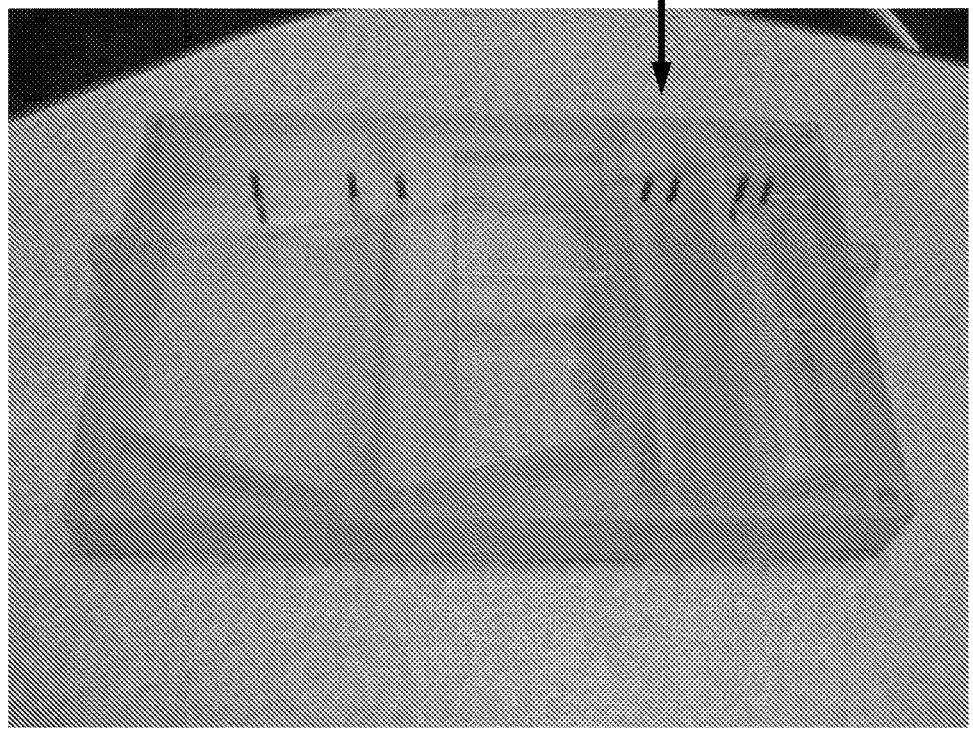
FIG. 11

1300

DEVICES FOR FLUID MANAGEMENT

CROSS REFERENCE TO RELATED APPLICATIONS

This is the U.S. National Stage of International Application No. PCT/US2015/052043, filed Sep. 24, 2015, which was published in English under PCT Article 21(2), which in turn claims the benefit of U.S. Provisional Application No. 62/054,843, filed Sep. 24, 2014; U.S. Provisional Application No. 62/160,510, filed May 12, 2015; and U.S. Provisional Application No. 62/212,268, filed Aug. 31, 2015, all of which are incorporated herein by reference in their entirety.

ACKNOWLEDGMENT OF GOVERNMENT SUPPORT

This invention was made with government support under Contract No. DE-AC52-06NA25396, awarded by the U.S. Department of Energy; and grant number R-00284-12-0, awarded by the Defense Threat Reduction Agency (DTRA). The government has certain rights in the invention.

FIELD

The present disclosure describes embodiments of devices for use with reactors requiring management of fluids flowing to and from a reactor system, and various components used therein. Also disclosed herein are embodiments of methods of making and using the devices.

BACKGROUND

Managing systems and/or reactors that require fluid delivery for operation can be complex and difficult, given, for example, the wide variety of components used in conventional reactor set-ups, the number of inlets and outlets required for fluid delivery, and the different types of fluids that can be required. Conventional manifolds or other conventional means for controlling fluid flow often require complex tubing configurations to facilitate and control fluid delivery to and from a reactor. Such complex set-ups are not user-friendly and often require a multitude of expensive components that have an increased margin of error during use. There exists a need in the art for devices and systems capable of reducing the complexity of fluid delivery mechanisms and the cost associated with such mechanisms.

Coupled systems of in vitro microfabricated organs-on-a-chip containing small populations of human cells are being developed to address the pharmacological and physiological gaps between monolayer cell cultures, animal models, and humans. These gaps present challenges not only in tissue and microfluidic engineering, but also in systems biology. For example, it must be determined how to model, test, and learn about the communication and control of biological systems at the scale of individual organs on chips. Allometric scaling provides some guidance, but appropriate biochemical and functional scaling of multiple organs and a universal cell-culture medium are also important to proper systems function and valid pharmacological interpretation.

Organ-on-a-chip technologies have advanced considerably in the past decade; however, understanding of biological scaling laws and how they apply to multiple, coupled organ devices has been largely ignored. To replicate human physiology and drug response with interconnected human organs-on-a-chip and larger human-like organ devices, each construct should have the correct relative size. Extensive literature describes differences in organ size between animal species whose body mass, M, spans 6 orders of magnitude. Organ size does not scale proportionally (isometrically) with M, but instead obeys a number of different allometric power laws that describe, for example, how as the animal's linear dimension L increases, its mass increases as $L^3$, and hence the cross-sectional area of the bones must increase out of linear proportion. Metabolic rates scale as $M^{3/4}$, blood circulation time scales as $M^{1/4}$, and pulmonary and vascular networks exhibit $M^{3/4}$ scaling (West et al., Science 276:122, 1997).

As organ devices are made smaller, scaling will ultimately fail, since individual cells have a fixed size, and immune cells, for example, function in isolation and at low densities. It is difficult to replicate the diameter of microcapillaries in tissue. The circulating volume of perfusate of an organ construct system must match organ size, lest metabolites, hormones, and paracrine signals be diluted to the point that each organ operates in a large reservoir independent of the other organs. Cellular heterogeneity, important to cellular signaling pathways in vivo, can be hard to maintain for long times in vitro. A universal media/blood surrogate is also needed to maintain multiple cell types, since most human cells are grown in media specific to the cell type and desired phenotype. Furthermore, devices should be mechanically and/or fluidly coupled and include sensing devices that can be used to evaluate the effects of compounds as they pass through each device.

SUMMARY

Disclosed herein are embodiments of devices comprising one or more channel substrates comprising one or more channels; a connection substrate comprising one or more inlets and/or outlets and one or more ports; and a valving system associated with the connection substrate comprising one or more valves positioned off-plane of the connection substrate and fluidly coupled to the one or more channels. In some embodiments, the one or more channels are microchannels, nanochannels, or large-sized channels. The valving system can comprise arch valves comprising a flexible material.

Also disclosed herein are embodiments of a reservoir, comprising one or more chambers for housing a fluid; one or more integrated flow channels located along one or more walls of the one or more chambers; and one or more ports for delivering fluid to or from the one or more chambers. In some embodiments, the one or more chambers comprise a readable scale for visually determining the amount of fluid in the chambers. The integrated flow channels can be formed within the one or more chambers.

Also disclosed herein are embodiments of a valving system for use with a fluid management device, comprising one or more flexible tubes capable of delivering fluid to channels of the fluid management device, wherein the flexible tubes form an arch configuration that extends off-plane from a connection substrate and wherein both ends of the flexible tubes are coupled to the connection substrate. In some embodiments, the valving system further comprises one or more valves capable of deforming the one or more flexible tube to restrict fluid flow through the flexible tube. In some embodiments, the one or more valves are selected from pinch valves, latching solenoid valves, or combinations thereof.

In additional embodiments, an integrated device is described (also referred to herein as an integrated fluid management device), comprising a fluid management device including one or more channel substrates comprising one or more channels; a connection substrate comprising one or more inlets and/or outlets; a valving system comprising one or more valves positioned off-plane of the connection substrate and fluidly coupled to the one or more channels; and a reservoir including one or more chambers for housing a fluid; one or more integrated flow channels located along one or more walls of the one or more chambers; and one or more ports for delivering fluid to or from the one or more chambers. In some embodiments, the integrated device can further comprise one or more reactors, such as a bioreactor. In yet additional embodiments, the integrated device can comprise one or more pumps.

Embodiments of a platform device are also described. The platform devices disclosed herein can comprise a bio-assessment device fluidly coupled to a fluid management device or an integrated fluid management device as described herein; an organ perfusion system in fluid communication with a fresh media circuit and a recirculation circuit, wherein the fresh media circuit is coupled to an inlet of the bio-assessment device through the fluid management device and the recirculation circuit is fluidly coupled an outlet of the bio-assessment device through the fluid management device; one or more rotary peristaltic pumps capable of pumping fluid to one or more rotary planar valves; a perfusion controller coupled to the organ perfusion system; and optionally an analyzer, a sensor, or a combination thereof coupled to the perfusion controller. In some embodiments, the bio-assessment device used with the platform device is a lung organ device. In any or all of the above described embodiments, the platform device can comprise a plurality of bio-assessment devices, wherein each bio-assessment device is fluidly coupled to a fluid management device or an integrated fluid management device as disclosed herein. In any or all of the above embodiments, the plurality of bio-assessment devices can be selected from a heart device, a liver device, a kidney device, a gastrointestinal device, a vascular device, a neuronal device, or a combination of two or more. In any or all of the above embodiments, the platform device can further comprise one or more microformulators fluidly coupled to the fresh media circuit and the recirculation circuit. In any or all of the above embodiments, the platform device can further comprise an analyzer, a sensor, or a combination thereof coupled to the perfusion controller The foregoing and other objects, features, and advantages of the present disclosure will become more apparent from the following detailed description, which proceeds with reference to the accompanying figures.

BRIEF DESCRIPTION OF THE DRAWINGS

FIG. 1A is an exploded perspective view of a fluid management device embodiment illustrating exemplary substrates that can be used to construct the exemplary fluid management device; FIG. 1B is a top perspective view of an exemplary connection substrate; FIG. 1C is a top perspective view of an exemplary channel substrate; and FIG. 1D is a top perspective view of another exemplary channel substrate.

FIGS. 4A-4E are top plan views illustrating fluid flow through an exemplary channel substrate; FIG. 4A illustrates fluid flow through the channels of the channel substrate during a seeding stage; FIG. 4B illustrates fluid flow through channels of the channel substrate during a feeding stage; FIG. 4C illustrates fluid flow through channels of the channel substrate during a circulating stage; FIG. 4D illustrates fluid flow through channels of the channel substrate during a sampling stage; and FIG. 4E illustrates fluid flow through channels of the channel substrate during a medium waste removal stage.

FIG. 10 is a perspective view of an exemplary reservoir assembly that can be used with the fluid management device embodiments disclosed herein.

FIG. 11 is a photographic image of an exemplary reservoir assembly.

DETAILED DESCRIPTION

I. Explanation of Terms

Figure 1A:
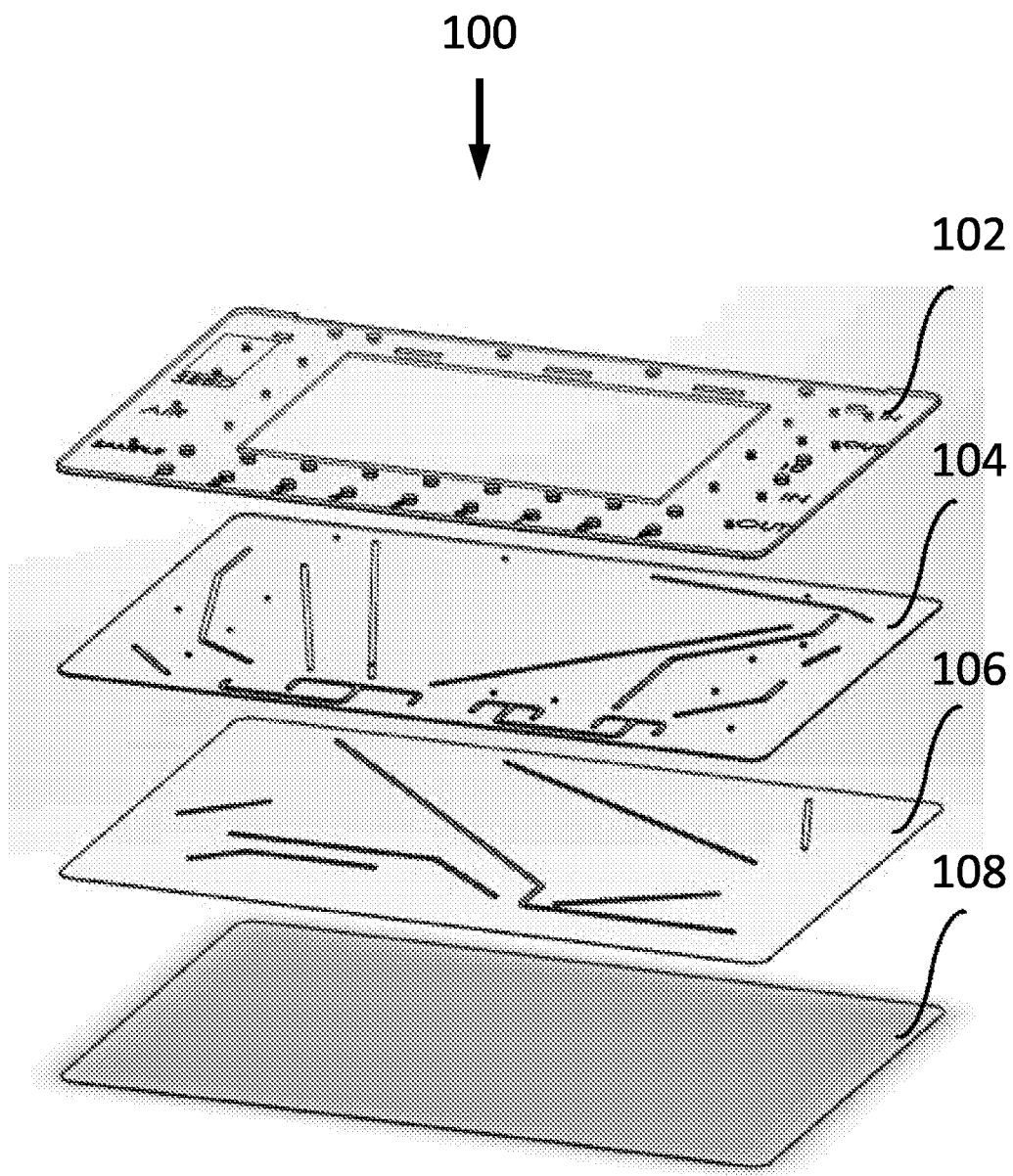
FIGS. 1A-1D illustrate the components of an exemplary fluid management device.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise. All references cited herein are incorporated by reference in their entirety.

Any theories of operation are to facilitate explanation, but the disclosed devices, materials, and methods are not limited to such theories of operation. Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed components and materials can be used in conjunction with other components and materials. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or devices are referred to as "lowest," "best," "minimum," or the like. It will be appreciated that such descriptions are intended to indicate that a selection among many used functional alternatives can be made, and such selections need not be better, smaller, or otherwise preferable to other selections.

Examples are described with reference to directions indicated as "above," "below," "upper," "lower," and the like. These terms are used for convenient description, but do not imply any particular spatial orientation.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

II. Introduction

Reactors, such as bio-assessment devices used for in vitro/ex vivo bioanalysis and/or other types of reactors, typically require complex fluid management mechanisms to facilitate transport, collection, and direction of fluids that flow to and from such reactors. The term "fluid management," as used herein, refers to the control of fluid transport to and from various components of a reactor system, control of fluid transport within a single component of a reactor system, and/or fluid transport through a platform device as disclosed herein. Bio-assessment devices and other reactor systems typically must be fluidly coupled to a variety of reservoirs, filters, pumps, and other components. Additionally, multiple modes of operation are utilized during use of the reactor, such as flow-based sterilization, washing, priming bio-assessment devices with media, cell seeding, drug introduction, sample collection, media exchange, waste withdrawal, and the like. All of these various components therefore must be reliably fluidly connected to the bio-assessment device or platform device (or other reactor) and the operational modes must be reliably controlled. Conventional methods for fluidly connecting components to bio-assessment devices (or other reactors) typically include using a network of tubing. Such networks, however, are very complex and typically require a large number of tubes having a variety of different lengths that can impede the ability to produce compact, portable devices for analysis. Also, complex tubing networks can often suffer in performance due to potential clogging, leaking, and/or kinking of the tubes. Furthermore, complex tube networks are not user-friendly and often can be difficult to set-up and or modify when needed before, during, or after use, often causing a large margin of error. Conventional fluid networks also require various reservoirs comprising different fluids—these reservoirs, when provided individually, contribute to the complexity of reactors and can also cause issues that reduce efficiency.

The device components disclosed herein provide the ability to facilitate fluid delivery to and from reactors (e.g., bio-assessment devices, chemical synthesis reactors, bag fermenters, and the like) and/or platform devices in a user-friendly, cost-efficient manner. While certain embodiments described herein are indicated for use with bio-assessment devices, some independent embodiments contemplate using the devices with other types of reactors requiring fluid management (e.g., reactors used in chemical synthesis, actinide processing, or other reactors used in combination with conventional manifold technology). The device components disclosed herein are capable of being integrated together with a bio-assessment device and/or component of a platform device as described herein to provide a compact system that is readily set-up, operated, and modified. The fluid management device components do not use complex tube networks and avoid the use of multiple separate reservoirs. The device components can be easily integrated into a working system without complex set-ups and are easily tuned to the particular reactor or platform device being used. In some embodiments, the devices can be integrated with external pneumatic systems used in reactor or platform device set-ups.

Also disclosed herein are embodiments of a platform device that can be used in combination with one or more fluid management devices (or integrated fluid management devices) disclosed herein to couple bio-assessment devices (also referred to as "organ devices") mimicking organs, such as a lung, kidney, liver, heart, or the like. The platform device comprises a plurality of components that help facilitate fluid communication between each bio-assessment device and its associated fluid management device (or integrated fluid management device). The platform devices and the fluid management devices (or integrated fluid management devices) can be used to deliver and monitor various drugs and/or toxins as they pass through each bio-assessment device included within the platform thereby providing the ability to evaluate the efficacy of new drugs and/or the deleterious effects of toxins on the organs.

III. Fluid Management Device Components

The components disclosed herein can be used to form systems (e.g., integrated fluid management devices) for managing fluid flow in reactors. Such systems can comprise fluid management devices, valving systems, reservoirs, and pumps that can be coupled to reactors to control fluid flow. The fluid management devices can be associated with valving systems and further fluidly connected to reservoirs containing the fluids to be introduced into the fluid management device. Pumps also can be connected to the fluid management device to produce desired flow rates of the fluid throughout the system.

A. Fluid Management Device

Disclosed herein are embodiments of fluid management devices comprising a channel network that facilitates compact integration of the device with a variety of reactors. In some embodiments, a multi-layer channel network can be provided (e.g., two or more layers of substrates comprising channels as described herein). The fluid management devices described herein are fabricated using cost-efficient materials, thereby providing components that are readily manufactured and do not contribute to increased costs associated with reactor operation.

Fluid management devices described herein are planar (or substantially planar) devices that are thin, compact, and utilize minimal external connections. In some embodiments, the fluid management devices are planar substrate devices comprising an optional base substrate, one or more channel substrates, and a connection substrate. In some embodiments, two or more channel substrates can be included in the fluid management device. In yet other embodiments, no channel substrates are needed and only a base substrate and connection substrate are provided. In yet other embodiments only a connection substrate is needed. The number of base and/or channel substrates used in the fluid management device can be modified according to the type of reactor to which it is fluidly coupled. Solely by way of example, a plurality of channel substrates (e.g., two or more, three or more, four or more, and so on) can be used to provide an increased number of flow channels that can be fluidly connected to one or more reactors or other components described herein. The substrates of the fluid management device can be made from a material suitable for laser ablation channel formation. In some embodiments, the substrates are formed from a biocompatible material. In some exemplary embodiments, the substrates are formed from polymeric materials selected from, but not limited to polydimethylsiloxane (PDMS), and/or acrylic or polycarbonate materials. In some embodiments, the substrates can have the same thickness, or progressively increasing thicknesses. Substrate thicknesses can range from 1 µm to 2 mm, such as 1 µm to 1 mm, or 1 µm to 0.5 min. In exemplary embodiments, the substrate thickness can be selected from 1 µm, 100 µm, 200 µm, 0.2 mm, 0.5 mm, and 1 mm.

In particular disclosed embodiments, the base substrate and/or optional channel substrates are fabricated to comprise flow channels that are fluidly coupled to provide a multi-layer channel network. In some embodiments, some or all of the channels can be fluidly coupled together. The channels can be micro-sized channels (e.g., microchannels), nano-sized channels (e.g., nanochannels), large-sized channels, or combinations thereof. The term "microchannels," as used herein, is understood to refer to channels having dimensions less than 1 mm and greater than or equal to 1 µm. The term "nanochannels," as used herein, is understood to refer to channels having dimensions less than 1 µm and greater than or equal to 1 nm. In yet other embodiments, the channels can be large-sized channels having dimensions less than 10 mm and greater than or equal to 1 mm. The channel dimensions can be modified according to the reactor to which the fluid management device is coupled. For example, fluid management devices comprising large channels (e.g., channels having dimensions less than 10 mm channels and greater than or equal to 1 mm) can be coupled to high-volume reactors (e.g., 1 or more liters). In yet other examples, fluid management devices comprising microchannels and/or nanochannels can be coupled to lower-volume reactors (e.g., under 1 liter, such as microliter-, nanoliter-, or milliliter-scale reactors). In some exemplary embodiments, microchannels having dimensions of 2 µm to 10 µm can be used, such as 5 µm to 10 µm.

Each substrate can comprise a plurality of channels and each substrate can have a different number of channels. The channels of each substrate can have the same or different dimensions. In some embodiments, the channels can have configurations that differ with each substrate. In some embodiments, the substrates include a plurality of channels that are fluidly coupled to one another when the device is assembled by stacking the substrates on top of each other. FIG. 1A illustrates exemplary channel shapes and configurations of the substrates that can be used for the medium-compatible component.

The substrates also can comprise one or more inlets, outlets, ports or combinations thereof. The connection substrate of the fluid management device comprises inlets and outlets through which fluids can be delivered to and from the fluid management device. Certain inlets and outlets are coupled to ports that extend from the planar surface of the connection substrate and allow for physical connection between tubes and the connection substrate. Using these inlets and outlets, fluids are delivered between the fluid management device and the reactor(s), reservoirs, and/or pumps (e.g., peristaltic pumps) to which the fluid management device is fluidly coupled. The connection substrate also comprises two or more inlets that are fluidly coupled to a valving system connected to the fluid management device to control flow of fluids through the fluid management device and the various components connected thereto. The valves of the valving system are discussed in more detail below. In some embodiments, the feed holes that are fluidly coupled to the valves are aligned along one side of the connection substrate; however, other suitable alternative configurations can be used.

Figure 1B:
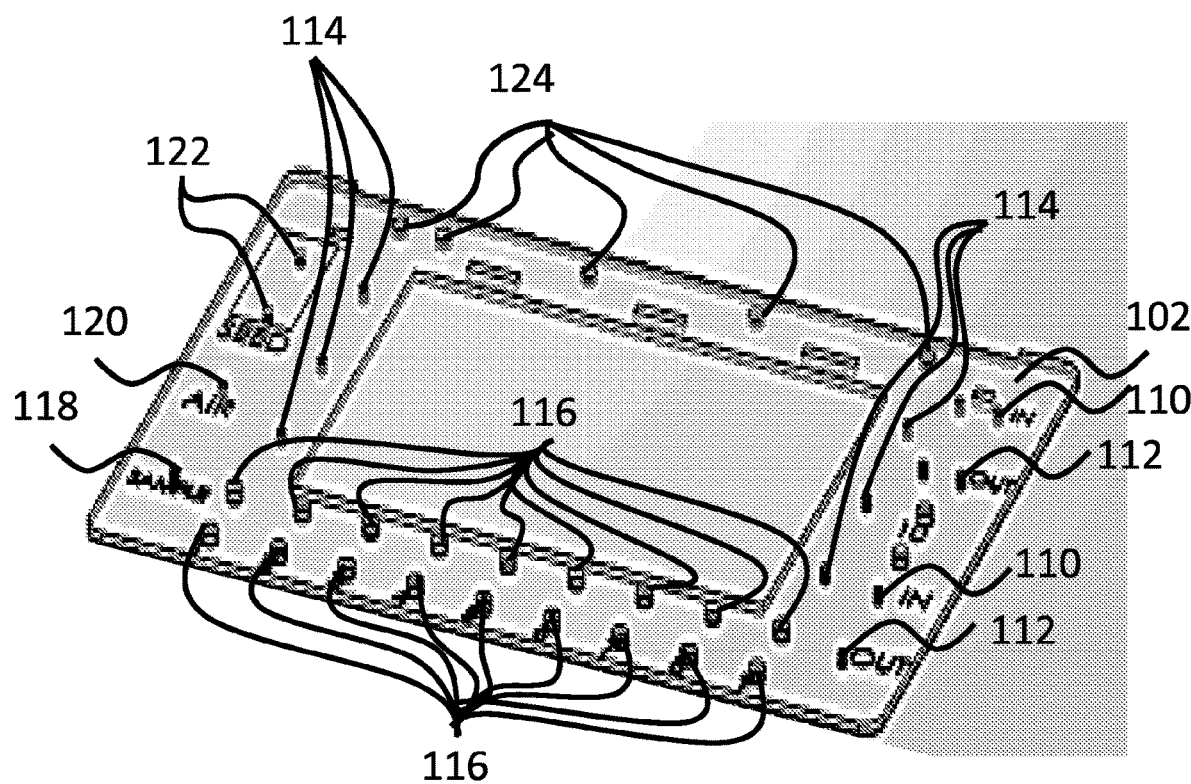

FIG. 1A illustrates an exemplary fluid management device 100. As illustrated in FIG. 1A, exemplary fluid management device 100 comprises a plurality of substrates, such as connection substrate 102, channel substrates 104 and 106, and base substrate 108 that are stacked so as to align the various channels, inlets, and outlets formed in the substrates. FIG. 1B illustrates an exemplary connection substrate 102 comprising a plurality of inlets 110, 116, 118, 120, 122, and 124 through which various fluids (e.g., air, biological media, liquid, or the like) can be introduced into the fluid management device 100. Inlets 116 can be coupled to a valving system, such as the arch valves discussed below (not illustrated in FIG. 1B). Typically, a pair of inlets are coupled together with tubing to form the arch valves and one of the inlets is used to deliver fluid from certain channels of an integrated channel network to the arch valve and one of the inlets is used to deliver fluid from the arch valve to a reactor through other certain channels of the integrated channel network. Connection substrate 102 further comprises one or more seed feed inlets 122 through which cells can be introduced into the bio-assessment device used in combination with the fluid management device, as well as an air inlet 120 and a sample inlet 118.

Figure 1C:
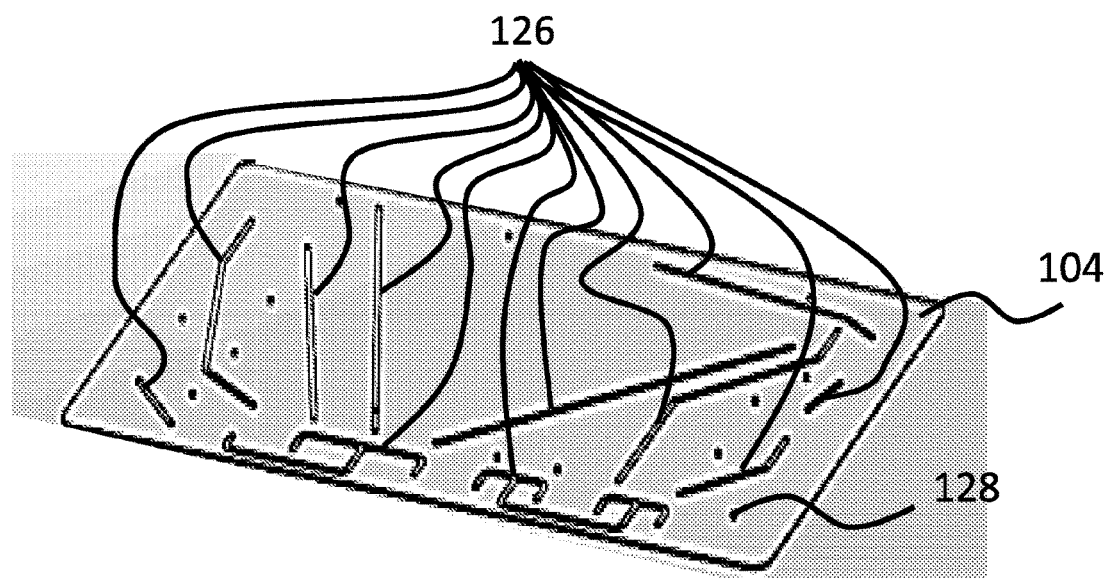
Figure 1D:
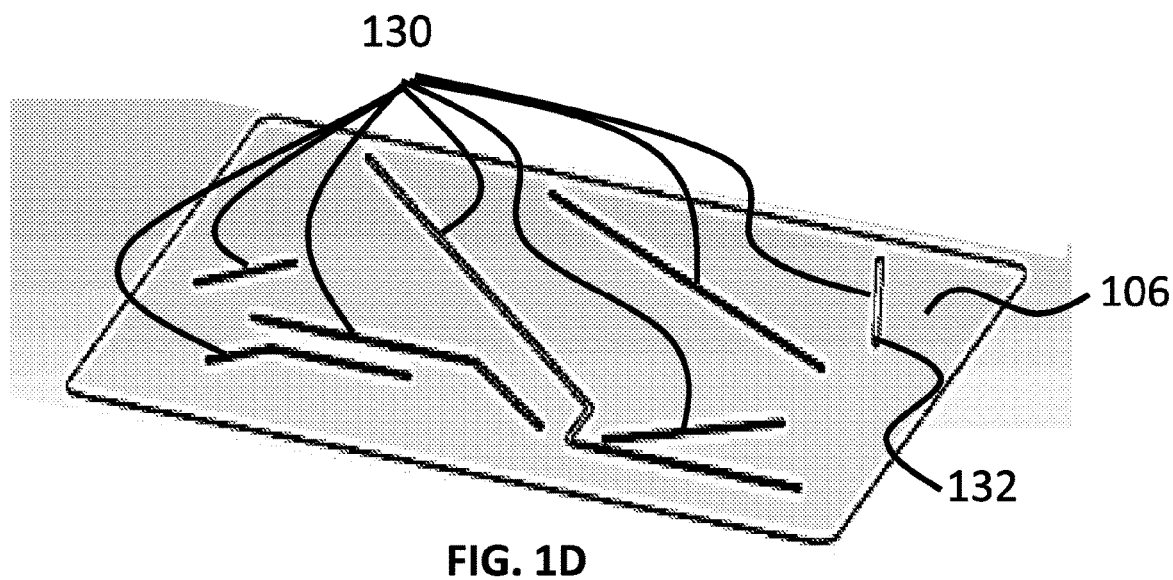

While the particular embodiment illustrated in FIGS. 1A and 1B depicts a particular configuration, other embodiments of the fluid management device can comprise alternate configurations of inlets, outlets, ports, valves, and channels, including more or fewer such components. Additional substrates comprising an integrated channel network also can be included in the fluid management device, such as channel substrates 104 and 106, illustrated in FIGS. 1C and 1D, respectively. Channel substrate 104, illustrated in FIG. 1C, comprises a plurality of channels 126 and inlets/outlets 128, which are used to deliver fluids introduced into the fluid management device to the reactor(s) to which the fluid management device is fluidly coupled. As indicated herein, channels 126 may have the same or different configuration and/or dimensions. Inlets/outlets 128 also can have the same or different size and/or shape. FIG. 1D illustrates another exemplary channel substrate 106 comprising additional channels 130 and a plurality of inlets/outlets 132. Channel substrates 106 and 104 are positioned so that the plurality of inlet/outlets 132 align with the plurality of inlet/outlets 128 of channel substrate 104 to thereby fluidly coupled channels 130 and 126.

Figure 2:
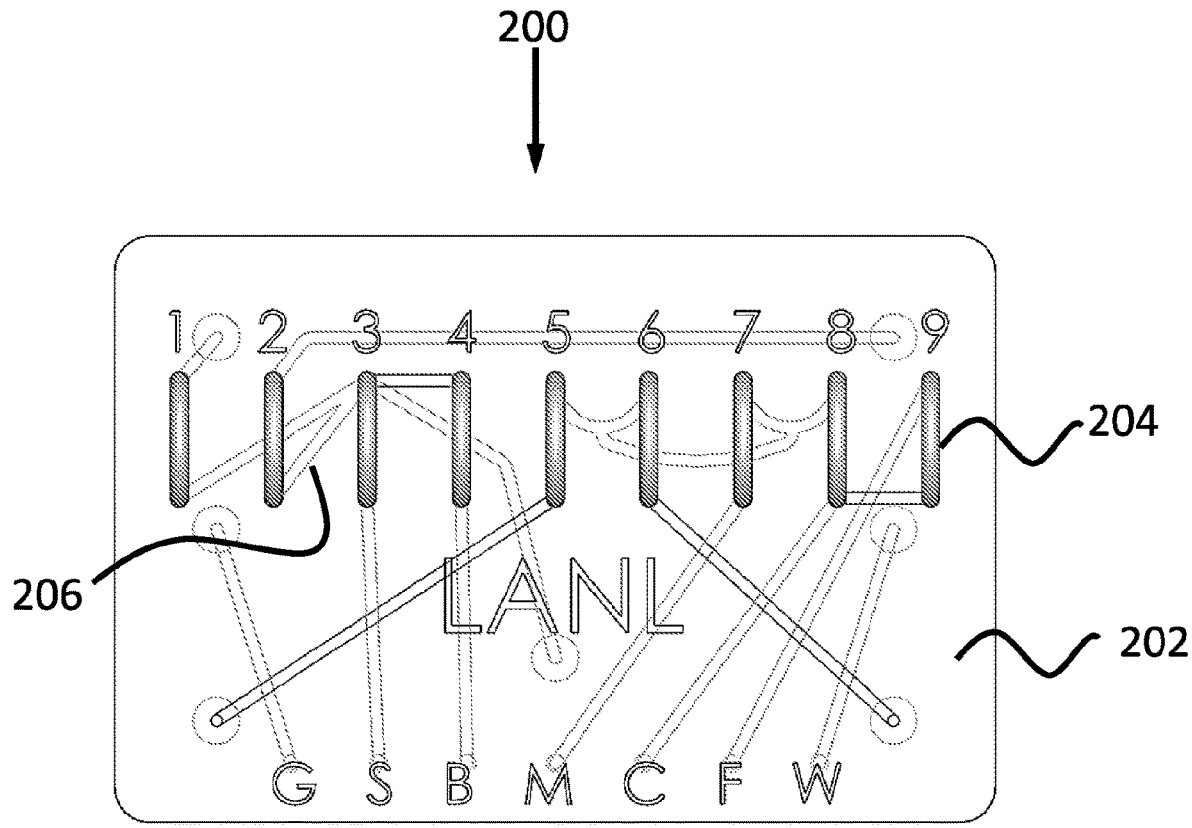
FIG. 2 is a top plan view of an exemplary constructed fluid management device.

FIG. 2 illustrates a top plan view of an exemplary connection substrate embodiment 202 of a fluid management device. As illustrated in FIG. 2, a plurality of arch valves 204 can be used to control flow into and out of flow channels 206 of the fluid management device 202.

Figure 3:
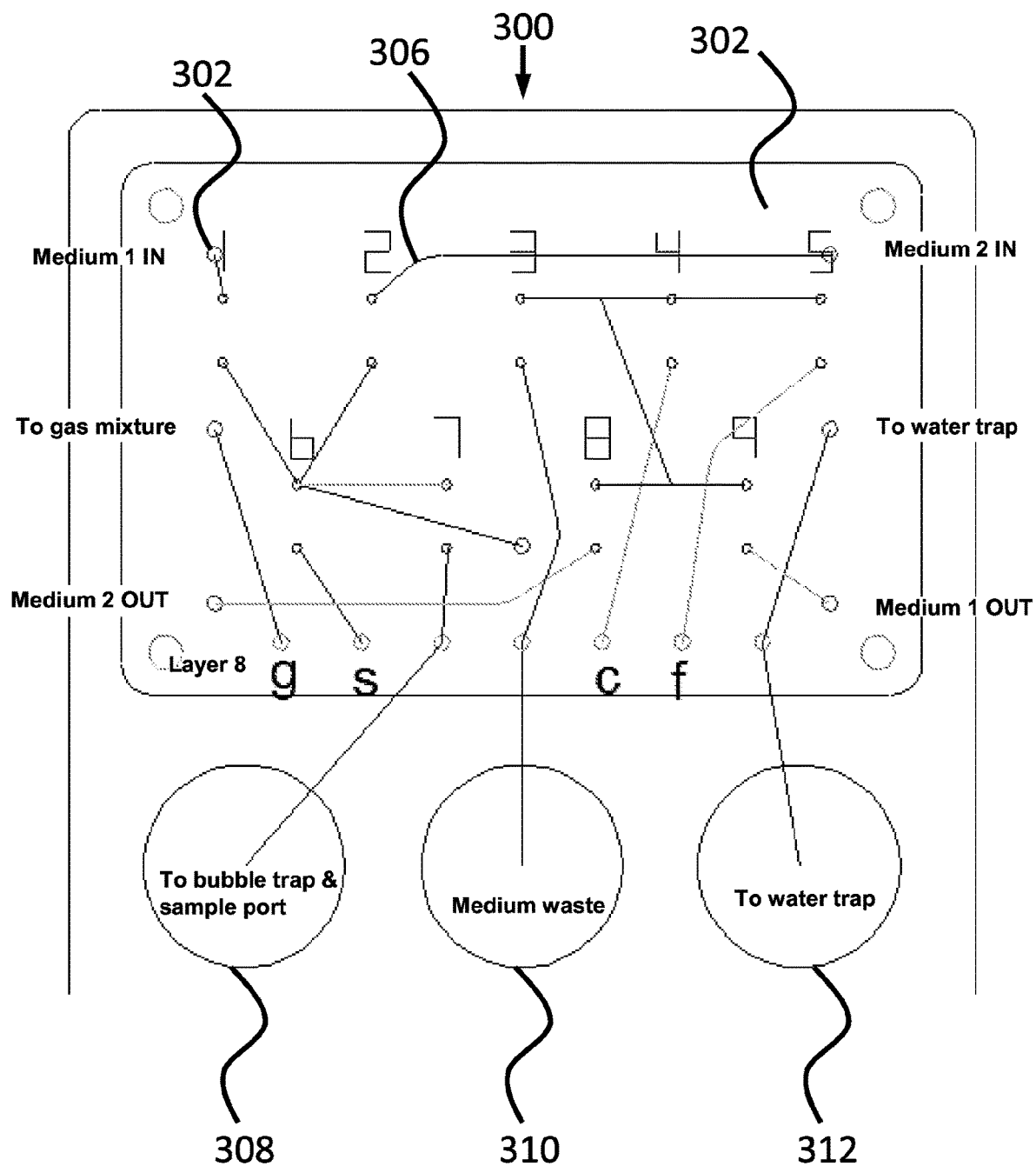
FIG. 3 is a top plan view of an exemplary substrate comprising a plurality of channels and inlets/outlets for delivering fluids through the fluid management device, and further illustrating reservoir chambers that can be coupled to the fluid management device.

FIGS. 3 and 4A-4E illustrate additional exemplary channel configurations that can be used. As illustrated in FIG. 3, multiple channels 306 can be fluidly coupled to multiple inlet/outlets 304 present on substrate 302 of the fluid management device 300. Connections, such as tube connections can be used to connect the fluid management device 300 to chambers 308, 310, and 312 of a reservoir (not illustrated) that is positioned adjacent to the fluid management device.

Figure 4B:
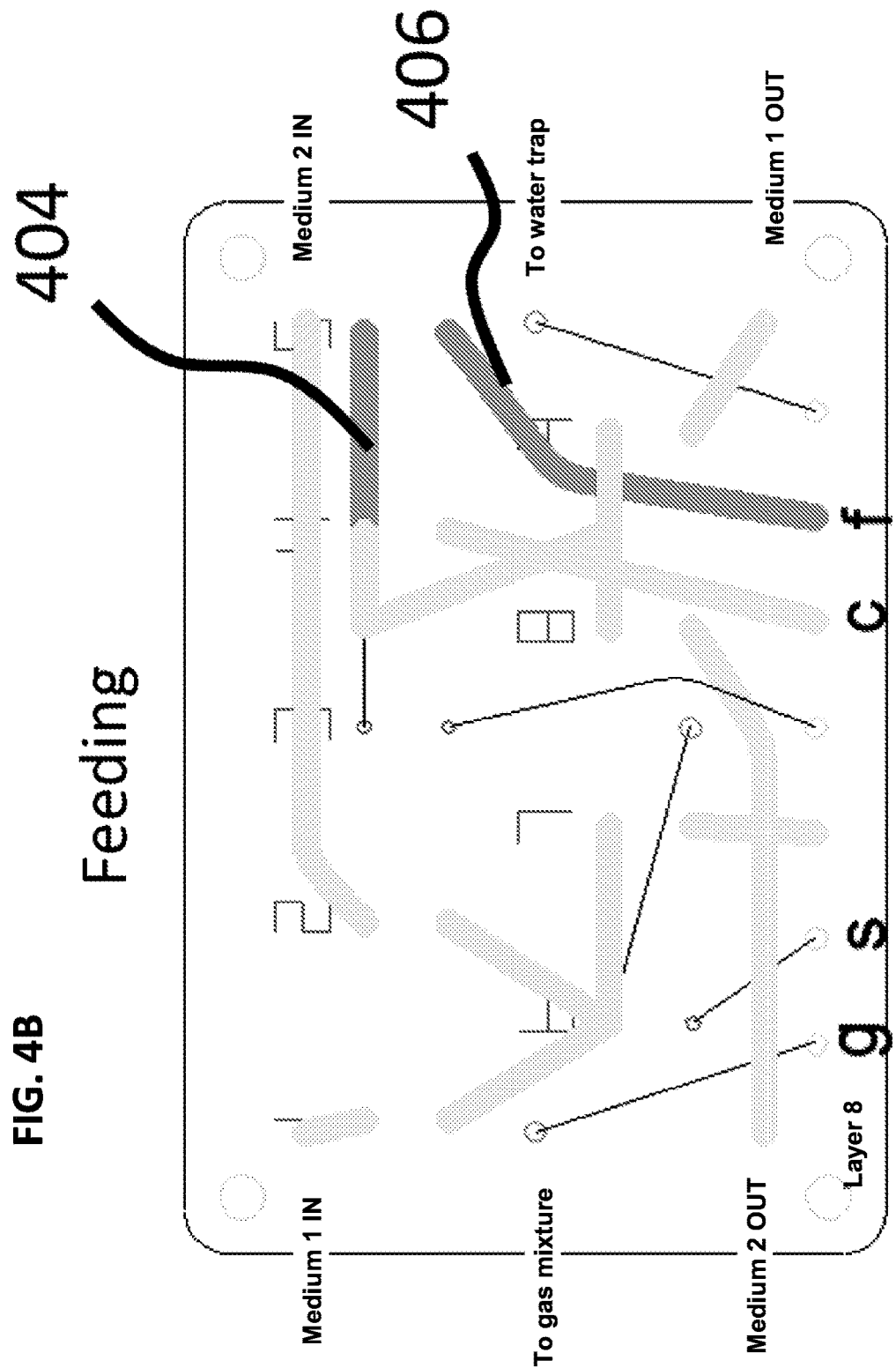
Figure 4D:
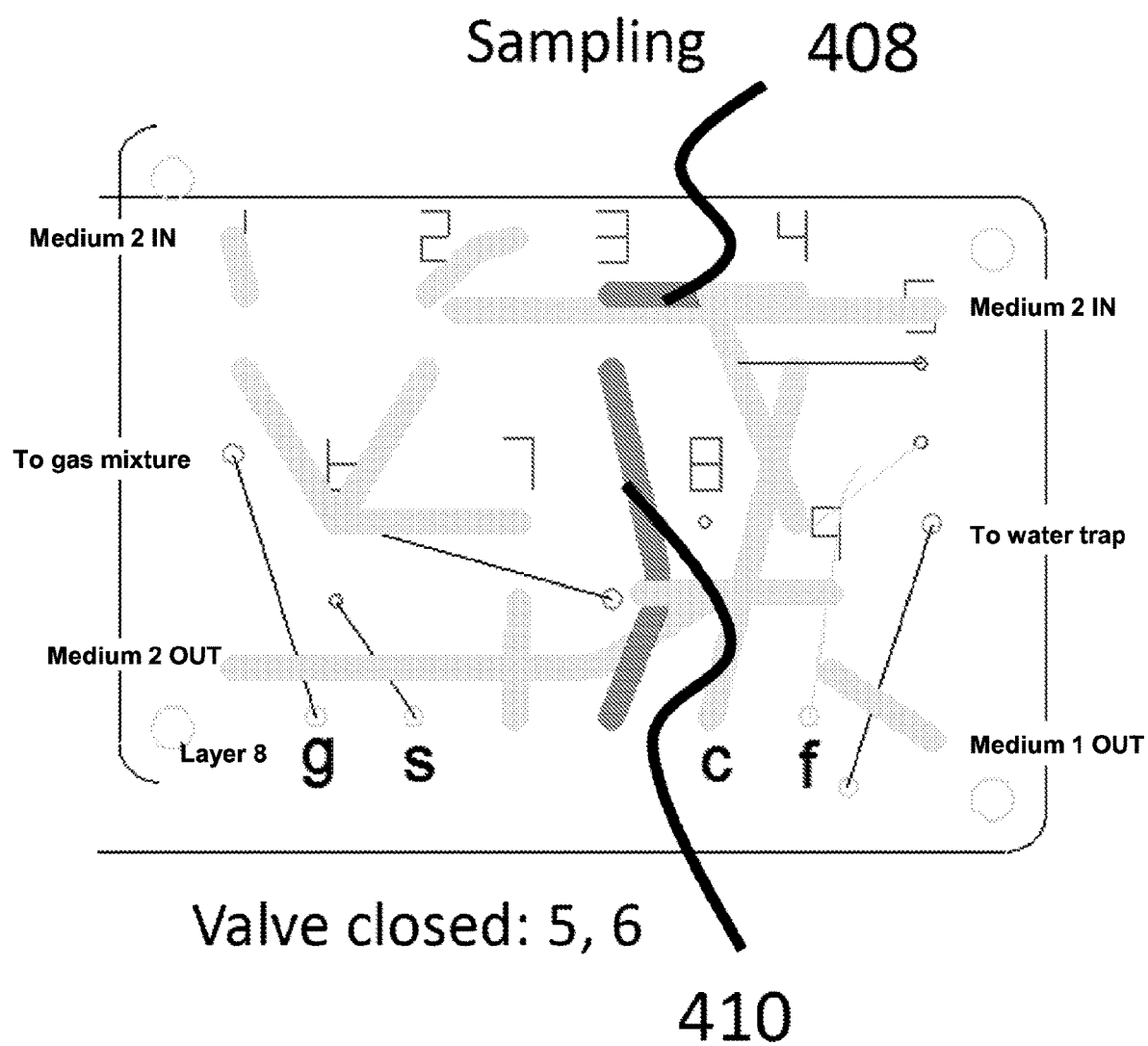

FIGS. 4A-4E illustrate fluid flow paths through an exemplary fluid management device substrate according to the different stage of operation being applied to an ex vivo bio-assessment device used for biological testing. FIG. 4A illustrates fluid flow (lines 400 and 402 indicate the seeding fluid flow as seeding cells are introduced into the fluid management device) through the fluid management device's channel network during seeding of an ex vivo bio-assessment device. FIG. 4B illustrates fluid flow through the fluid management device as a feeding operation is used (lines 404 and 406 indicate the feeding fluid flow as a feeding medium is introduced into the fluid management device) and FIG. 4C illustrates fluid flow as fluids are circulated through the ex vivo bio-assessment device. A sampling fluid flow scheme is illustrated in FIG. 4D (lines 408 and 410 indicate the sampling fluid flow as a sample is withdrawn from the fluid management device) and waste removal is illustrated in FIG. 4E (lines 412 and 414 indicate the waste fluid flow as waste is removed from the fluid management device). Also, with reference to FIGS. 4A-4E, "G" refers to a gas mixer flow channel, "S" to a seeding flow channel, "B" to a bubble trap flow channel, "M" to a medium waste flow channel, "C" to a circulating flow channel, "F" to a feeding flow channel, and "W" to a water trap.

Figure 5:
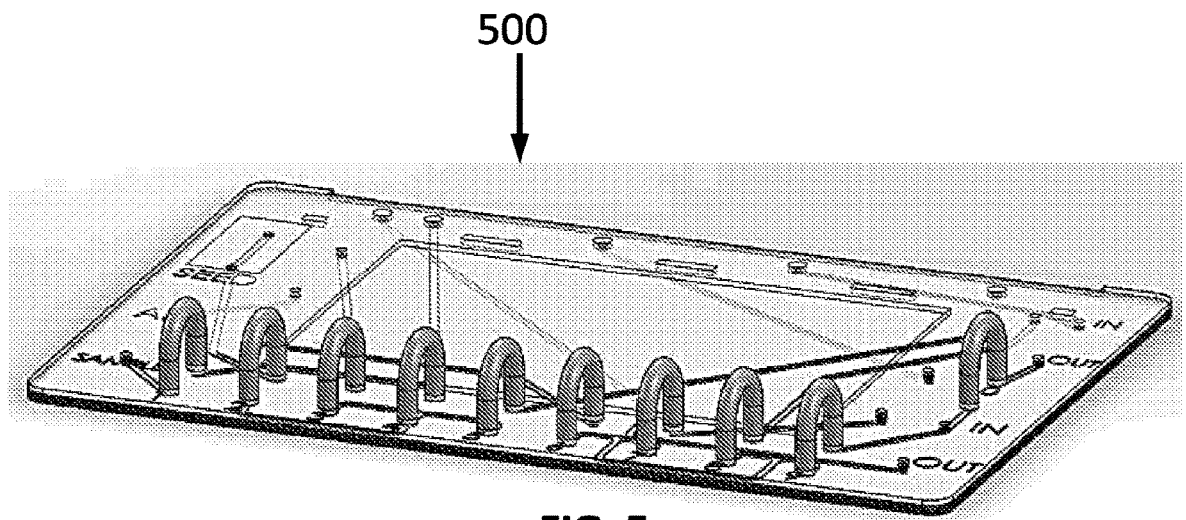
FIG. 5 is a perspective view of another exemplary fluid management device.
Figure 6:
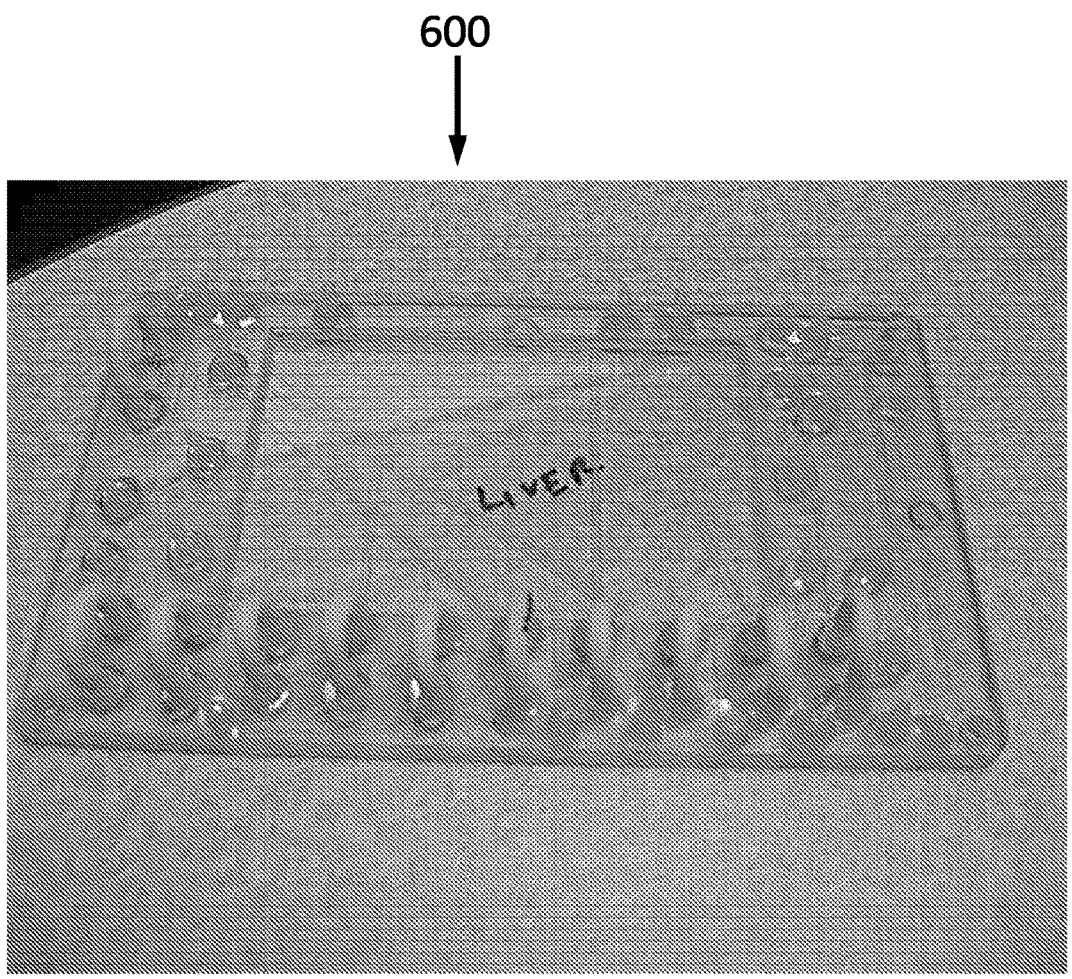
FIG. 6 is a photographic image of an exemplary fluid management device.
Figure 7:
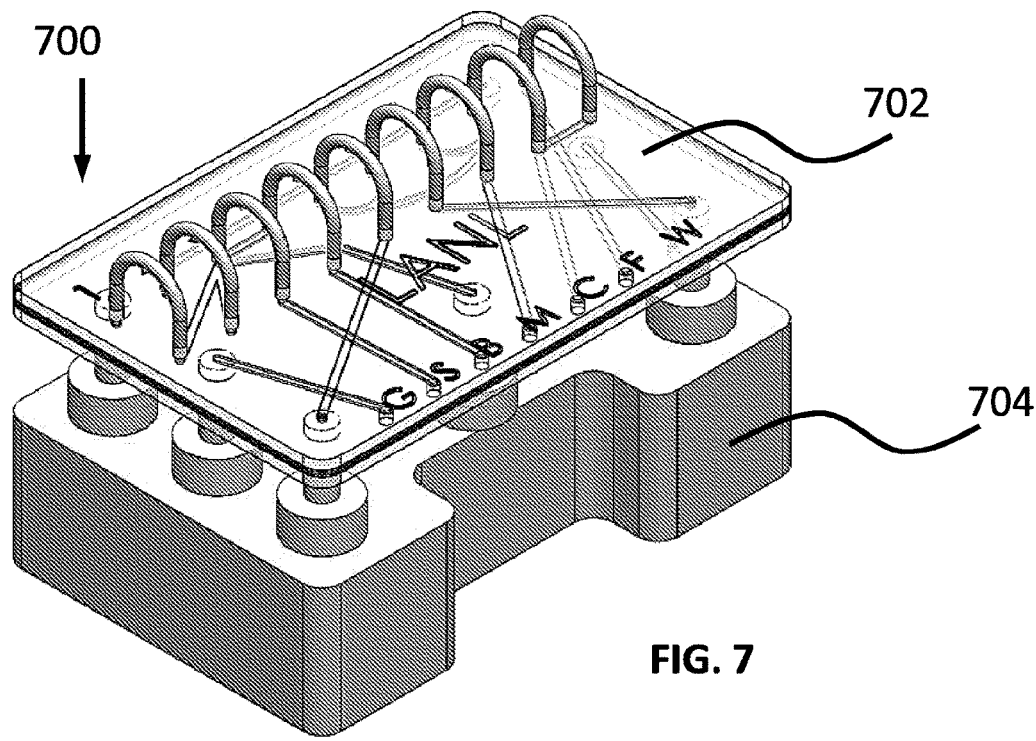
FIG. 7 is a perspective view of an exemplary integrated bio-assessment device/fluid management device.
Figure 8:
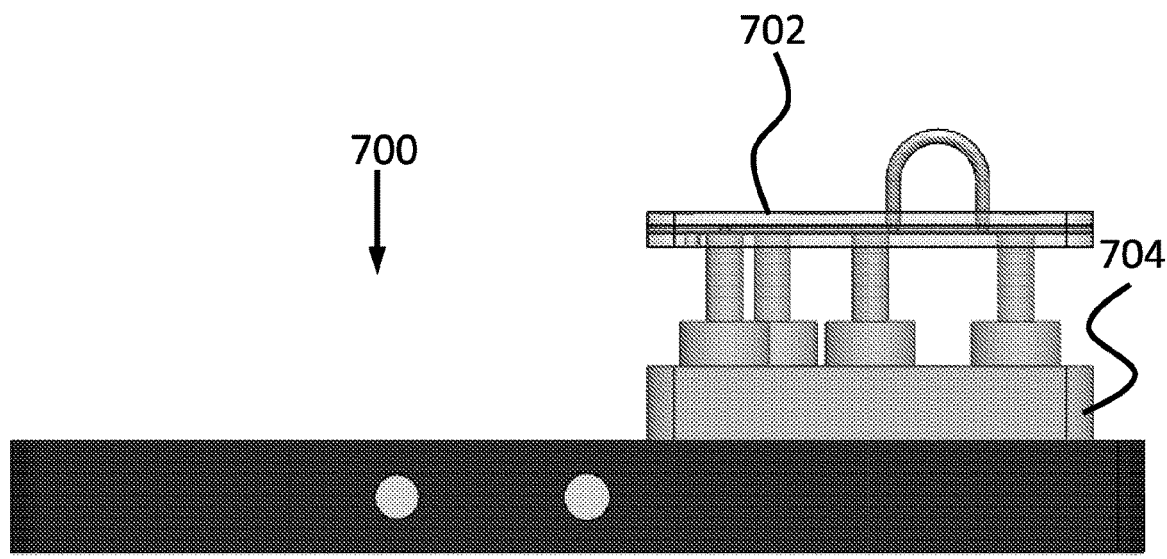
FIG. 8 is a side view of the exemplary integrated device construct illustrated in FIG. 7.

Another exemplary fluid management device 500 is illustrated in FIG. 5. FIG. 6 provides a photograph of a constructed embodiment 600. FIGS. 7 and 8 illustrate embodiments of an integrated device 700 comprising a fluid management device 702 coupled to a bio-assessment device 704.

While certain figures described herein illustrate exemplary fluid management devices for use with bio-assessment devices, the fluid management devices contemplated by the present disclosure can be modified to include additional ports, inlets, outlets, and/or channels to facilitate using a network of integrated reactors (e.g., a system of ex vivo bio-assessment devices, such as a liver bio-assessment device, a lung bio-assessment device, a heart bio-assessment device, a kidney bio-assessment device, or any reactors disclosed in U.S. Patent Application Publication Nos. 2015/0004077, 2012/0003729, 2011/0294202 or 2006/0099705, each of which is incorporated herein by reference; or a system of other reactors, such as chemical synthesis reactors, fermenters, and the like). Additionally, the fluid management devices disclosed herein can be modified for use in commercial reactors in pre-existing set-ups using conventional tube networks to manage fluid flow. For example, the disclosed fluid management devices are designed to be readily integrated with commercial reactors so that the complex tube networks and/or reservoirs can simply be disconnected and replaced with the fluid management device and other components disclosed herein.

In some embodiments, fluid management devices for use with heart bio-assessment devices (also referred to as a "heart device(s)" and/or "left heart device" and/or "right heart device") are described. Such fluid management devices can comprise one or more of the channel substrates described herein, wherein the channel substrates are configured to comprise a plurality of channels suitable for delivering fluids to and from various ports (e.g., inlets and/or outlets) of the heart devices. For example, heart devices can comprise one or more media inlets and outlets, one or more gas inlets and outlets, and one or more cell inoculation inlets. Each of these inlets and outlets can be fluidly coupled a corresponding outlet and inlet of a fluid management device through the channels of the channel substrates so that fluids can pass into and out of the heart device. In some embodiments, a right heart device can be used that comprises a corresponding fluid management device (or integrated fluid management device) having inlets and outlets that can be aligned and fluidly coupled with inlets and outlets of the right heart device through a plurality of channels formed within channel substrates of the fluid management device. A valve system can be included with the fluid management device to control pumping of fluid from the right heart device to a lung organ device. In additional embodiments, a left heart device can be used that comprises a corresponding fluid management device (or integrated fluid management device) having inlets and outlets that can be aligned and fluidly coupled with inlets and outlets of the left heart device through a plurality of channels formed within channel substrates of the fluid management device. A valve system can be included to control pumping of fluid from the left heart to a kidney and/or liver device. In yet additional embodiments, a left heart device and a right heart device can share a fluid management device (or integrated fluid management device), which is configured to comprise inlets and outlets that can align with inlets/outlets of each of the right heart device and left heart device through a plurality of channels.

In some embodiments, fluid management devices (or integrated fluid management devices) can be used in combination with kidney bio-assessment devices (also referred to as "kidney devices"). In some embodiments, a fluid management device (or integrated fluid management device) used with a kidney device can comprise one or more inlets and one or more outlets that are fluidly coupled with one or more inlets and one or more outlets of the kidney device (e.g., blood surrogate inlets and outlets and glomerular filtrate inlet and outlets) via a plurality of channels formed within the channel substrate(s) of the fluid management device. The fluid management device can further comprise a valve system that is used to control flow to the kidney device from other bio-assessment devices and/or the fresh media circuit and flow from the kidney device to other bio-assessment devices and/or the recirculation circuit.

B. Valves

The devices disclosed herein comprise unique valving systems that facilitate delivering the various fluids delivered through the fluid management device to and from the reactor, the reservoir, and one or more pumps. The valving systems described herein provide the ability to modify connections and/or control flow into the channel network of the fluid management device without having to disassemble the fluid management device to access the channel network of a base substrate (and/or optional channel substrates). Furthermore, fluid flow through the fluid management device and the reactor(s) can be controlled via simple manipulation of the valves of the valving system, such as by deforming (e.g., pinching) the valves closed and then allowing the valves to reform (e.g., by unpinching) to allow flow to continue.

In some embodiments, the valves are arch valves that extend off-plane from the planar substrate and are connected to at least two inlets of the connection substrate. In some embodiments, the valves comprise a flexible material, such as tubing material known to those of ordinary skill in the art. In some embodiments, the flexible material is biocompatible. In some embodiments, the valves can be controlled using mechanical, magnetic, and/or pneumatic systems. In exemplary embodiments, the valves are arch valves that can be used in combination with other separate valves that facilitate control of the arch valves, such as pinch valves, latching solenoid valves, or combinations thereof. In some embodiments, these valves can be controlled manually or they can be automated.

Figure 9:
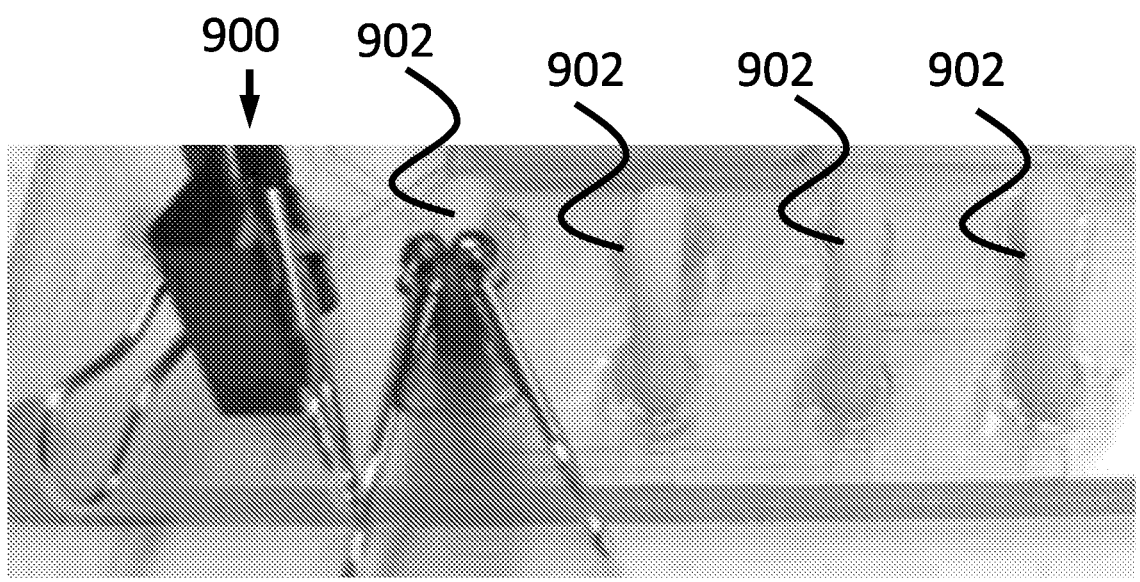
FIG. 9 is a photographic image of a portion of the exemplary fluid management device shown in FIG. 6 illustrating a zoomed view of exemplary arch valves used with the fluid management system.

The valves can be connected to the fluid management device by ports that are coupled to the surface of the connection substrate. These ports are associated with inlets of the connection substrate and therefore are fluidly coupled to the channels of the integrated channel network. A single valve can be used, or a plurality of valves can be used depending on the type of reactor. Exemplary valve set-ups are illustrated in FIGS. 5-8. A zoomed photographic image of an exemplary valving system 900 comprising arch valves 902 is provided by FIG. 9. This figure also illustrates exemplary manipulation of the valves by pinching, using a simple clip.

C. Reservoirs

Also disclosed herein are embodiments of reservoirs that are used in combination with the fluid management devices described herein. In some embodiments, the reservoirs are used to store fluids that are first delivered to the fluid management device and then are delivered to the reactor(s) or bio-assessment device(s) for chemical and/or biological processes, such as cell/tissue culture inside the reactor and/or titration. In other embodiments, the reservoirs also are used to store waste that is produced by using the reactor(s) or bio-assessment device(s). The reservoirs disclosed herein can be fabricated as an integrated component comprising multiple reservoirs (such as one or more fluid storage reservoirs and/or one or more waste reservoirs). This capability provides an advantage over conventional reservoirs, which typically are separated/isolated chambers that each require a separate tubing set-up to facilitate fluid delivery. Separate chambers can cause issues with set-up, are not user-friendly, and can require extraneous space and components that increase operation and fabrication costs. In contrast, the presently disclosed reservoirs are made using durable, cost-efficient materials, can be easily removed from (or integrated with) the reactor set-up, and are compact.

Figure 18:
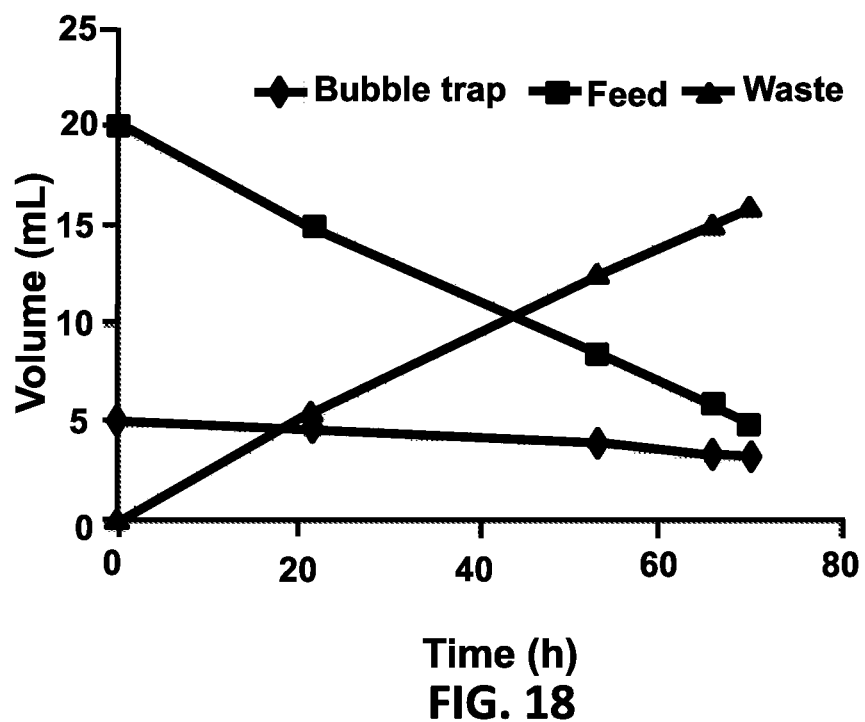
FIG. 18 is a graph of volume (mL) as a function of time (hours) the volumes of liquids present in different chambers of an exemplary reservoir assembly over hours of continuous operation.

In particular embodiments, the reservoirs disclosed herein comprise one or more chambers that are separated from one another and that are each configured to contain a volume of fluid. In particular disclosed embodiments, the reservoirs comprise a plurality of chambers. In exemplary embodiments, a reservoir comprises a chamber that functions as a bubble trap, a chamber that functions as a water trap, a feed chamber, and a waste chamber. Each chamber can be configured to comprise a readable scale on the chamber wall. The readable scale can be used to visually determine the amount of fluid present in the chambers of the reservoir. In yet additional embodiments, one or more chambers of the reservoirs can be configured to comprise membranes, such as gas permeable membranes to accommodate diffusion of gases produced by or introduced into the reactor without permitting fluid to pass through the membrane. The chambers also can comprise sensors that can be used to detect changes in, for example, fluid level, pH, gas concentration, and the like. Fluid levels can then be graphed according to the length of operation of the device, such as is illustrated in FIG. 18.

In some embodiments, the feed and waste chambers can hold 20 mL or more of fluid, such as greater than 0 mL to 20 mL, or greater than 0 mL to 25 mL, or greater than 0 mL to 30 mL or more. The size of the reservoir, however, can be modified to provide chambers holding more or less liquid. Flow rates of the fluids can be controlled so as to deliver a particular amount of fluid from the feed chamber to the fluid management device. In some embodiments, flow rates of 3 µL/minute to 5 µL/minute can be used. Reservoir size and flow rates can be scaled up or down, depending on the reactor size or volume utilized.

In some embodiments, the reservoirs comprise integrated flow channels to facilitate delivery of the fluids to and from the various chambers of the reservoir. The integrated flow channels can be positioned along the walls of the reservoir chambers so as to reduce the amount of space required by the reservoir and to reduce the complexity of tubing connected to the reservoir. The integrated flow channels also are fluidly coupled to inlets and outlets that are used to deliver fluid to and from the reservoir's integrated flow channels to the reactor(s). The integrated flow channels can be directly fabricated in the reservoir using laser ablation techniques. In some embodiments, the reservoir can further comprise a plurality of ports that can be used to refill and/or extract the fluids in chambers of the reservoir. In some embodiments, these ports are positioned on the side of the reservoir opposite to that which is connected to the fluid management device. Thus, a user is able to refill and/or empty the chambers of the reservoir even while the device is in use without having to remove the reservoir from its location and/or disconnect tubing connecting the reservoir to the fluid management device.

An exemplary reservoir is illustrated in FIG. 10. As illustrated in FIG. 10, reservoir 1000 comprises four chambers, a bubble trap chamber 1008, a water trap chamber 1006, a feed chamber 1004, and a waste chamber 1002.

Reservoir 1000 further comprises integrated channels 1010 that facilitate fluid flow from the reservoir between chambers of the reservoir and to and from a fluid management device. A plurality of ports 1012 also is provided to fluidly couple the chambers of the reservoir to the channel network of a fluid management device. An exemplary reservoir 1100 is also shown in FIG. 11.

D. Integrated Devices

The device components described herein can be integrated to form an integrated fluid management device. In particular disclosed embodiments, the fluid management device is fluidly coupled to a reservoir via one or more inlets present on the connection substrate. The inlets of the fluid management device can comprise ports to which tubes can be connected, which are also connected to inlets and/or outlets and ports present on the reservoir. The fluid management device can also be coupled to one or more of the valve systems disclosed herein to form an integrated fluid management device. In some embodiments, the integrated fluid management devices can further comprise integrated sensors that are used to monitor various different parameters associated with any chemical and/or biological processes that occur in the reactor. In yet other embodiments, an integrated fluid management device can comprise the fluid management device in combination with a valve system, a reservoir, and/or sensor(s) and further in combination with a bio-assessment device, such as those disclosed in International Patent Application No. PCT/US2015/052039, entitled "BIO-ASSESSMENT DEVICE AND METHOD OF MAKING THE DEVICE,", filed on Sep. 24, 2015, which is incorporated herein by reference. Additional bio-assessment devices, such as liver devices, kidney devices, and heart devices are described in U.S. Patent Application Publication No. 2014/0356849, and International Application Publication No. WO 2014/081840, each of which is incorporated herein by reference.

In some embodiments, the integrated fluid management device can further comprise one or more pumps connected to the fluid management device. The pumps can be used to cause fluid flow such as by pumping fluids to and from the reservoir of an integrated fluid management device. Some embodiments disclosed herein can use miniaturized pumps that are compact. In yet additional embodiments, the reactor can be coupled to all components of an integrated fluid management device via the integrated channel network of the fluid management device.

Figure 12:
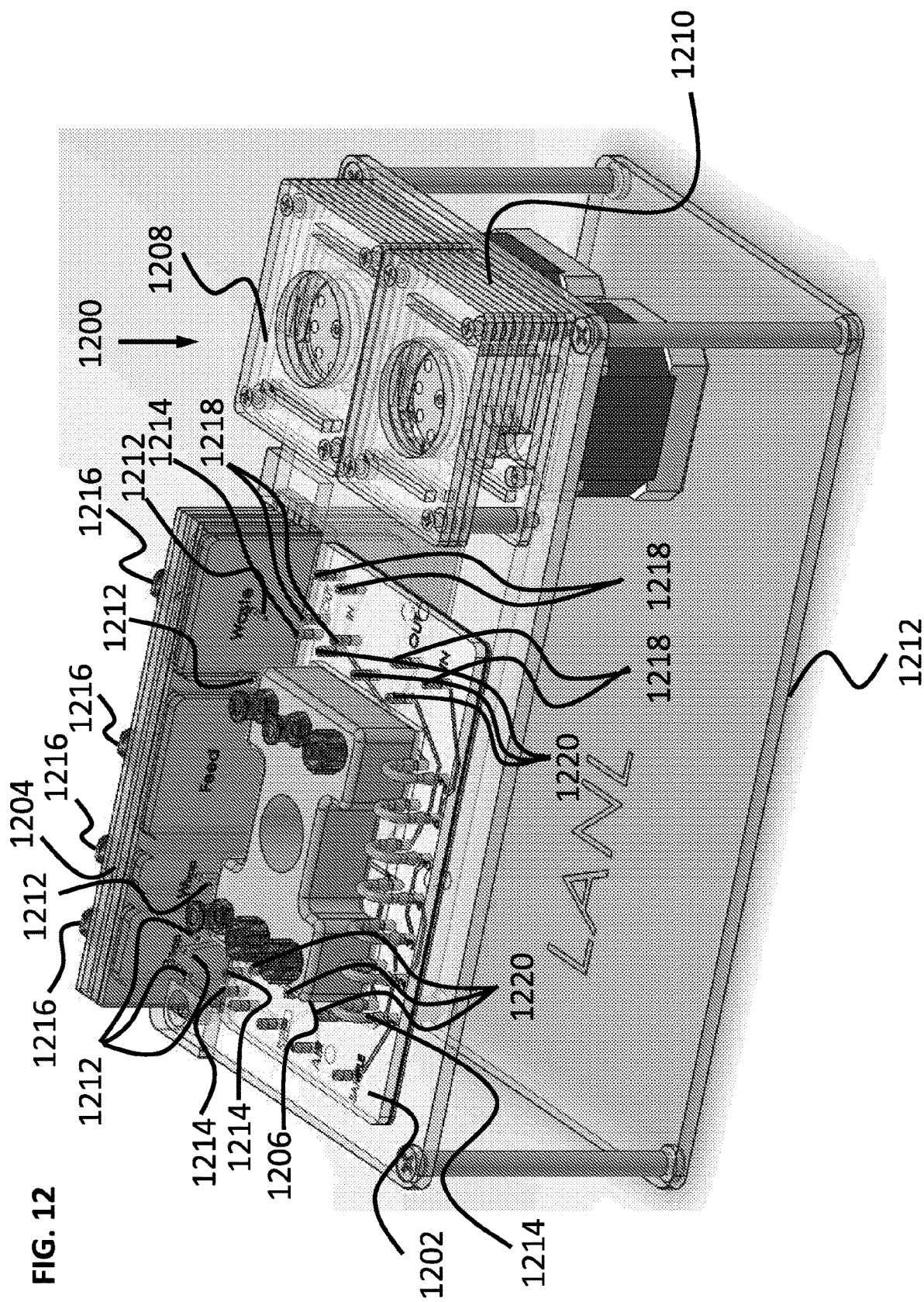
FIG. 12 is a perspective view of an integrated device comprising an exemplary fluid management device embodiment, an exemplary reservoir assembly embodiment, an exemplary bio-assessment device, and exemplary pumps.

Integrated fluid management devices disclosed herein are compact and easily modified to fit the needs of a user. An exemplary integrated device set-up is illustrated in FIG. 12. As illustrated in FIG. 12, integrated device 1200 comprises a fluid management device 1202 comprising a valving system with arch valves 1214, a reservoir 1204, and two miniaturized pumps 1208 and 1210. An exemplary bio-assessment device 1206 also is illustrated; however, any type of reactor can be utilized. Integrated device 1200 also comprises a platform 1212. Due to its compact size and planar configuration, fluid management device 1202 can be positioned below bio-assessment device 1210 and thus is conveniently located without requiring extraneous space and long tubing networks to connect to the bio-assessment device. In other embodiments, the fluid management device can be positioned above the bio-assessment device, such as illustrated in FIGS. 7 and 8.

Figure 13:
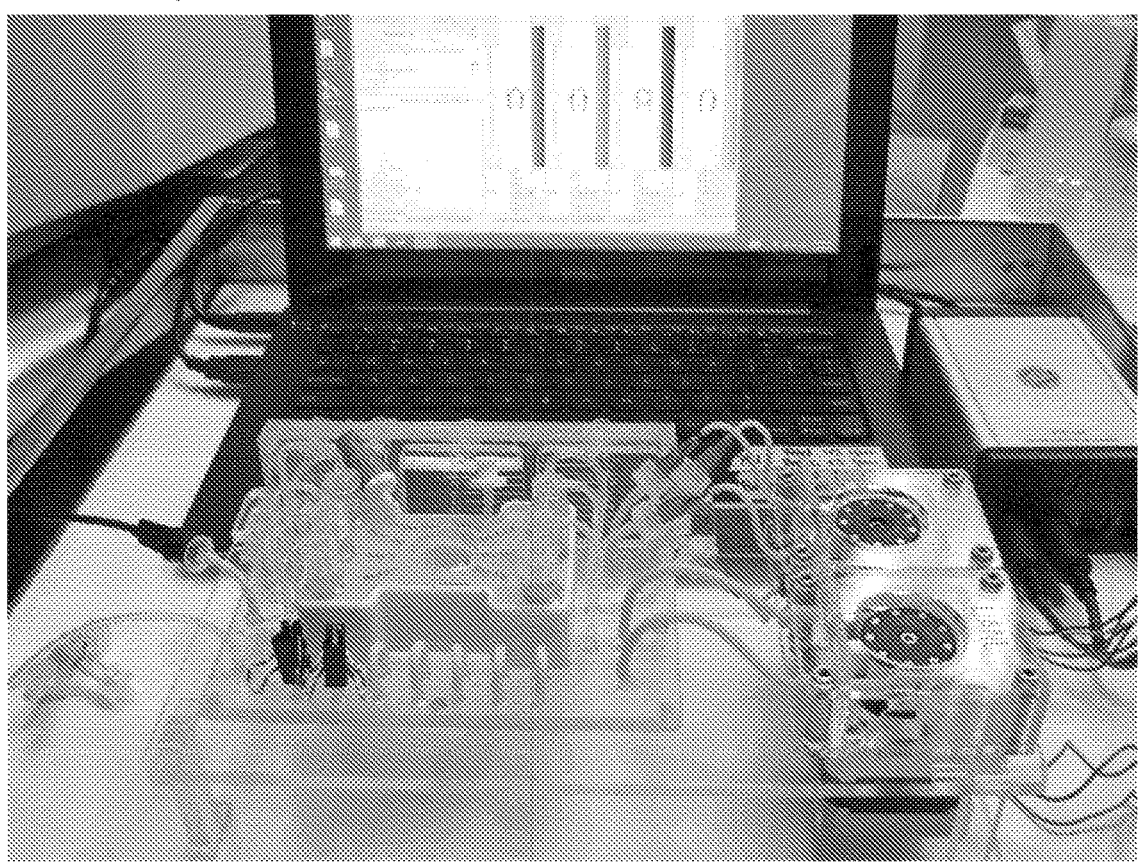
FIG. 13 is a photographic image of an exemplary integrated device comprising an exemplary fluid management device embodiment, an exemplary reservoir assembly embodiment, an exemplary bio-assessment device, and exemplary pumps.

As further illustrated in FIG. 12, the compact reservoir 1204 is conveniently located adjacent to the fluid management device 1202 such that ports 1212 of the reservoir can be fluidly coupled to ports 1214 of the fluid management system using short lengths of tubing. The reservoir 1204 also is positioned so that ports 1216, which are utilized to refill and/or remove fluids from the reservoir face away from fluid management device 1202 and are easily accessed by a user during use of the integrated device 1200. A valving system, such as the plurality of arch valves 1214 illustrated in FIG. 12, also is located adjacent to the bio-assessment device to facilitate delivery of fluids to the integrated channel network of the fluid management device 1202 that is conveniently located below bio-assessment device 1206. Miniaturized pumps 1208 and 1210 also are of a compact size so that they can be positioned adjacent the fluid management device 1202 without requiring long tube lengths for connection. Pumps 1208 and 1210 are connected to fluid management device 1202 via ports 1218. The integrated device 1200 illustrated in FIG. 12 can easily be modified in configuration and placement to facilitate use of any type of bio-assessment device and also can be scaled according to need (e.g., for use with high volume bio-assessment devices). In the embodiment illustrated in FIG. 12, bio-assessment device 1206 is fluidly coupled to ports 1220 of fluid management device 1202, which deliver fluids from the integrated channel network of the fluid management device, which is conveniently located below bio-assessment device 1206. FIG. 13 shows another exemplary integrated device 1300 and further shows the various connections that are used to integrate the fluid management device, reservoir, pumps, and bio-assessment device.

Figure 14:
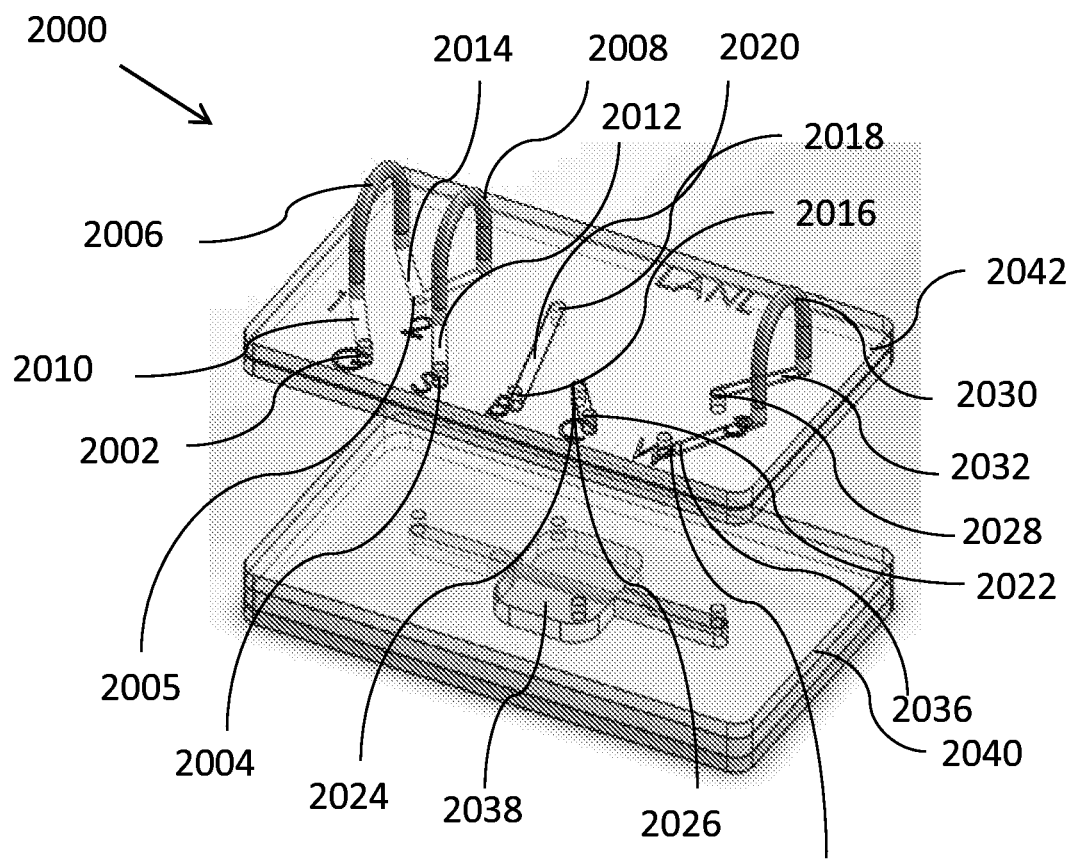
FIG. 14 illustrates an embodiment of a fluid circuit board that can be used with the lung organ device to control delivery of fluids into and out of the device.
Figure 15:
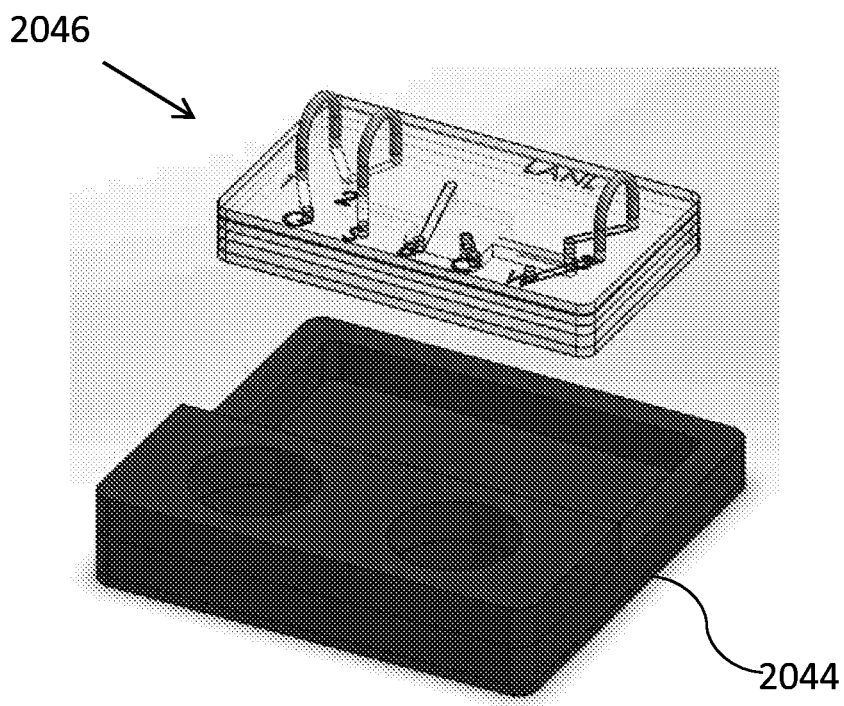
FIG. 15 illustrates an embodiment of a fluid circuit board connected to a bronchiolar device of the lung organ device and a holding stage that can be used with the device.
Figure 16:
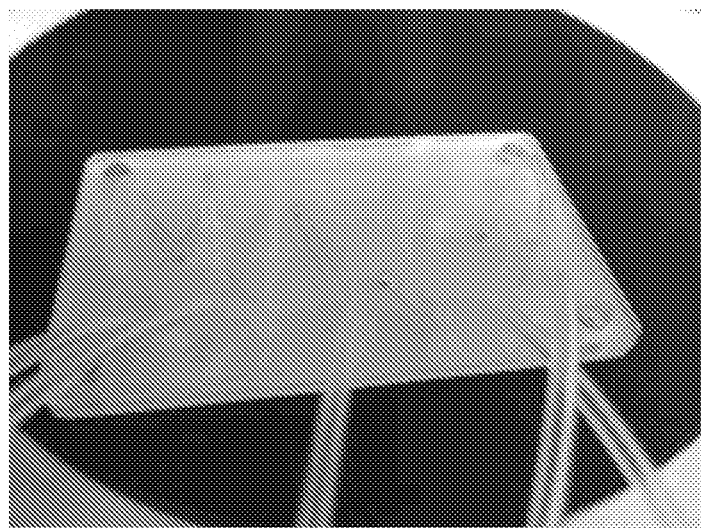
FIG. 16 shows a working example of the fluid circuit board illustrated in FIG. 14.
Figure 17:
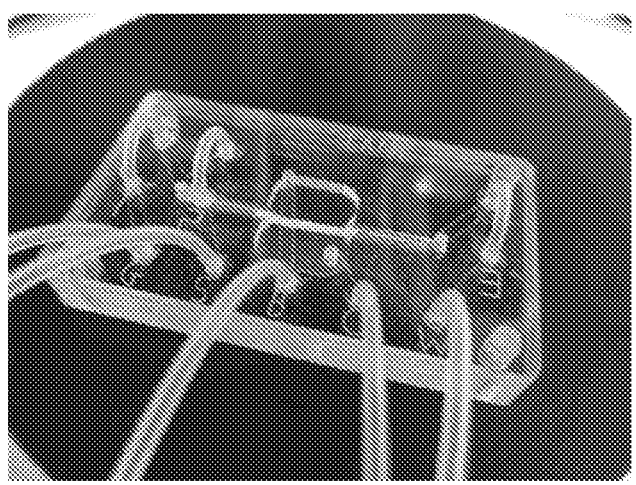
FIG. 17 shows a working example of a fluid circuit board combined with a bronchiolar device.

FIG. 14 illustrates another embodiment of an integrated fluid management device. According to the embodiment illustrated in FIG. 14, fluid management device 2000 can be fabricated as a polymeric substrate 2042 comprising, for example, an inlet 2002 through which a first fluid can be introduced in an exemplary bio-assessment device 2040, and a second inlet 2004 through which cells (or a composition thereof) can be introduced into the bio-assessment device. Inlets 2002 and 2004 can be fluidly coupled with channels 2010 and 2012, respectively, which can deliver fluid or cells to tube lines 2006 and 2008, respectively. Tube lines 2006 and 2008 are further fluidly coupled to V-shaped channel 2014, which is fluidly coupled to inlet 2005. Inlet 2005 can deliver the fluid or cells to bronchiolar device 2040. The fluid management device 2000 can further include an inlet 2016 through which a second fluid, such as a biological medium, can be introduced into an incubation chamber 2038 via channel 2020 and fluid port 2018 of bio-assessment device 2040. The second fluid can be delivered from the bio-assessment device 2040 via outlet 2022, which is fluidly coupled to fluid port 2026 via channel 2024. In some embodiments, the fluid management device 2000 includes an outlet 2034 from which the first fluid can be isolated for testing. Outlet 2034 can be fluidly coupled to the bioreator 2040 through channel 2036, which is fluidly coupled to tube 2030, channel 2032, and fluid port 2028. In exemplary embodiments, the fluid management device 2000 can be associated with the bio-assessment device 2040 and then coupled with holder 2044, as illustrated in FIG. 15 to form an integrated fluid management device. FIG. 16 shows an exemplary fluid management device and corresponding tubing and FIG. 17 shows an integrated device.

IV. Platform Devices

Disclosed herein are embodiments of a platform device that can be used to facilitate coupling and operation of a plurality of bio-assessment devices (such as 2, 3, 4, 5, or more bio-assessment devices) and their corresponding components. In some embodiments, the platform device can be used to control interactions between a plurality of bio-assessment devices and thereby couple such devices in a manner that allows fluid communication between the bio-assessment devices. In particular disclosed embodiments, the platform device is used to facilitate biological analysis using the plurality of bio-assessment devices and can thereby be used to evaluate the effects of biomedical drugs and/or toxic substances on particular organs of the body without having to administer the drugs in vivo. The platform device can be used in combination with a variety of different bio-assessment devices, each of which is a biomechanical construct of its corresponding human organ counterpart. For example, bio-assessment devices that can be used with the disclosed platform devices include, but are not limited to, lung devices (such as those disclosed in International Patent Application No. PCT/US2015/052039, entitled "BIO-ASSESSMENT DEVICE AND METHOD OF MAKING THE DEVICE,", filed on Sep. 24, 2015), heart devices, liver devices, kidney devices, or other organ devices (such as a vascular device or a neuronal device).

In particular disclosed embodiments, the platform device comprises a plurality of components that together function to control each bio-assessment device, evaluate operation of each bio-assessment device, and/or control and evaluate the effects of various substances administered into the integrated system. The platform device can comprise a combination of organ sensing and control instrumentation, such as, but not limited to, one or more of an organ perfusion system, an air supply, a fresh media circuit (e.g., an arterial system), a recirculation circuit (e.g., a venous system), a microformulator, rotary peristaltic pump(s), rotary planar valve(s), a perfusion controller, analyzer(s) and/or sensor(s), multi-channel potentiostat(s), electrode(s), and any combination of two or more thereof. In particular disclosed embodiments, the platform device can comprise one or more of the fluid management devices (or integrated fluid management devices) disclosed herein. Each of these components is discussed in more detail herein.

In some embodiments, the platform device is configured to fluidly couple the plurality of bio-assessment devices by including certain of the components described above and one or more fluid management devices (or integrated fluid management devices) as disclosed herein. The organ devices may be connected in parallel, in series, or a in a configuration combining parallel and serial relationships between the organ devices. In one exemplary embodiment, a heart device (which may include left heart and right heart components) is fluidly coupled to a lung device, a liver device, and a kidney device, each of which may comprise its own unique fluid management device (or integrated fluid management device). One or more of the heart, lung, liver, and kidney devices are fluidly coupled to a fluid management device (or integrated fluid management device), which in turn can be coupled to a fluid transport system including one or more reservoirs. The fluid transport system can be fluidly coupled to fluid inlets and outlets of the organ device(s) via the fluid management device (or integrated fluid management device).

In one exemplary embodiment, a platform device comprises an air supply component (e.g., a ventilator, an air tank, or the like) coupled to a lung organ device through a fluid management device (or integrated fluid management device), which in turn is fluidly coupled to a heart device via the lung organ device's fluid management device (or integrated fluid management device) and a heart fluid management device (or integrated fluid management device) fluidly coupled to the heard device. In some embodiments, the heart device can be a single heart device or a left heart device and a right heart device. A singular heart device (or a left heart device) can be fluidly coupled to a fresh media circuit (e.g., an arterial system) through the heart device's fluid management device (or integrated fluid management device), wherein the fresh media circuit comprises a separate reservoir containing arterial system fluids and/or other nutrients. The fresh media circuit is further fluidly coupled (directly or indirectly) to the fluid inlets of the liver device (or inlets of a liver device fluid management device or integrated fluid management device) and the lung organ device (or inlets of the lung organ device's fluid management device or integrated fluid management device), as well as the fluid inlets of one or more microformulators and/or missing organ microformulators, a kidney device, a perfusion controller, or a combination thereof. The heart device (or a right heart device) can be fluidly coupled to a recirculation circuit (e.g., a venous system) directly or through its corresponding fluid management device (or integrated fluid management device). The recirculation circuit can comprise a reservoir suitable for accepting fluids delivered from the various bio-assessment devices of the platform device. The recirculation circuit is further fluidly coupled (directly or indirectly through a corresponding fluid management device or integrated fluid management device) to the lung organ device, a liver device, the kidney device, the perfusion controller, the one or more microformulators, or a combination thereof.

Exemplary platform device configurations are provided in U.S. Patent Application Publication No. 2014/0356849, and International Application Publication No. WO 2014/081840, both of which are incorporated herein by reference. Any suitable configuration can be used to couple the bio-assessment devices of the platform device. For example, the bio-assessment devices, including the lung organ devices disclosed herein can be fluidly coupled in parallel, wherein fluid management devices (or integrated fluid management devices), such as those disclosed herein, provide the ability to control each of the bio-assessment devices present in the platform. In yet additional embodiments, one or more of the bio-assessment devices are fluidly connected in parallel, while one or more bio-assessment devices are connected in series. In such embodiments, the serially connected bio-assessment device(s) is coupled parallel to the bio-assessment devices that are connected in parallel. For example, a gastrointestinal organ device (or missing organ microformulator) can be positioned upstream from a liver organ device, and both of these organ devices can be coupled in parallel to a kidney organ device and one or more of a lung organ device and a heart device directly, or indirectly through one or more corresponding fluid management devices (or integrated fluid management devices). In another embodiment, a heart device can be fluidly coupled in series with a lung organ device, wherein the lung device is fluidly coupled in series to a single heart device, or fluidly coupled in series between both a right heart device and a left heart device. In some embodiments, the platform device provides the ability to bypass one or more bio-assessment devices within the platform device, for example for maintenance, sample collection, or to study the effects of removing one bio-assessment device from the system.

Figure 19:
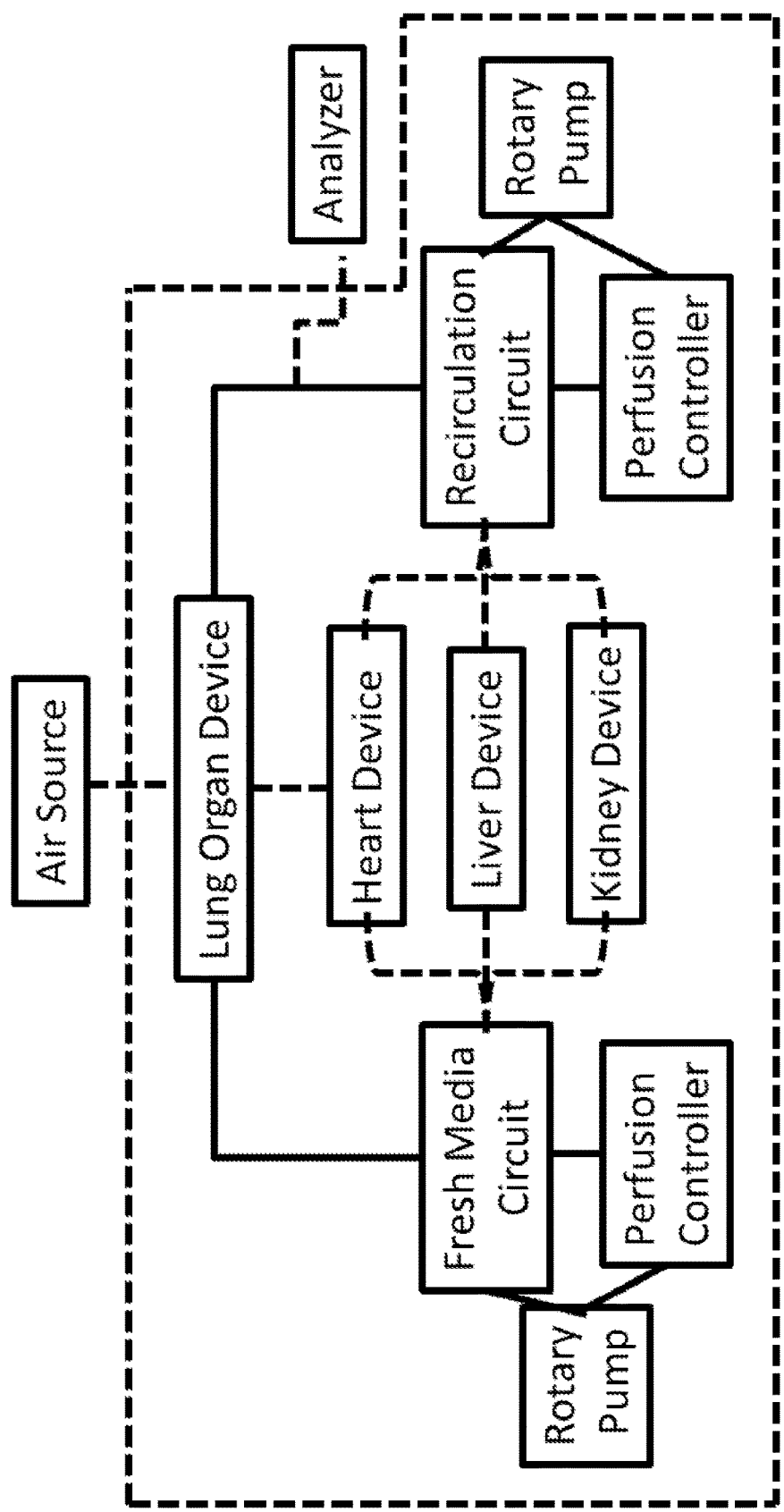
FIG. 19 is a schematic diagram of a representative embodiment of a platform device comprising a plurality of bio-assessment devices.

FIG. 19 is a schematic illustration of an exemplary platform device configuration comprising a lung organ device and a plurality of other optional bio-assessment devices. As illustrated in FIG. 19, an exemplary platform device embodiment can comprise an air source that can be coupled to a lung organ device, which in turn can be fluidly coupled to a heart device. The heart device and the lung organ device are coupled to a fresh media circuit, which can be further fluidly coupled to a liver device and a kidney device. The fresh media circuit also can be coupled to a multi-organ perfusion controller and one or more rotary pumps. As illustrated in FIG. 19, the lung organ device, and any other optional bio-assessment devices, can be coupled to a recirculation circuit, which can also be coupled to a perfusion controller and one or more rotary pumps. The platform device can also optionally include an analyzer which can be in fluid communication with the recirculation circuit, the perfusion system, and/or any of the bio-assessment devices. The embodiment illustrated in FIG. 19 is not intended to be limiting, but instead is provided as a representative embodiment to illustrate one possible way in which the components can be arranged using embodiments of the disclosed platform.

In particular disclosed embodiments, an organ perfusion system is used to control fluid flow throughout the platform device and the bio-assessment devices used with the platform device. In some embodiments, the perfusion system comprises a perfusion controller comprising a fluid management system (or integrated fluid management device) and one or more pumps capable of delivering perfusion fluids, nutrients, and/or biological media. In some embodiments, the organ perfusion system comprises a recirculation circuit (for example, a circuit that continuously circulates medium through the perfusion system) and a fresh media circulation circuit (for example, a circuit that introduces fresh medium into the perfusion system). The perfusion system can comprise one or more pumps that provide media recirculation (e.g., 3 to 300 mL/min) in the recirculation circuit, and fresh media (e.g., 0.5 mL to 50 mL/hr) from the fresh media circulation circuit to the bio-assessment devices. In some embodiments, the perfusion controller of the perfusion system can operate in different modes, such as a bypass control mode, a serial perfusion mode, and an organ replacement perfusion mode. In an embodiment of a bypass control mode, the perfusion controller is used to allow medium (such as blood surrogate or universal medium, examples of which are included in International Patent Application No. PCT/US2015/052046, entitled MULTI-ORGAN MEDIA COMPOSITIONS AND METHODS OF THEIR USE, filed on Sep. 24, 2015, which is incorporated herein by reference) to bypass a bio-assessment device, for example so that a different medium can be delivered to the bio-assessment device. In an embodiment of a serial perfusion mode, a bio-assessment device, which is in a serial configuration with one or more bio-assessment devices, is perfused in series with the other bio-assessment devices. In an embodiment of an organ replacement perfusion mode, a bio-assessment device is removed from the platform device and therefore isolated from other bio-assessment devices of the platform device. Flow through the platform device is maintained by utilizing fluid management devices (or integrated fluid management devices) of the bio-assessment devices, particularly the valves associated with the fluid management devices (or integrated fluid management devices). A component for analysis, such as a drug, toxin, or other compounds or agents, can then be introduced into the isolated bio-assessment device for evaluation and analysis. In this manner, the effect of one or more compounds on the particular bio-assessment device can be evaluated without exposing other bio-assessment devices to the compound(s). The perfusion system can be fluidly coupled to other components of the platform device and/or the bio-assessment devices or components of the bio-assessment devices. In some embodiments, the perfusion system is fluidly coupled to a recirculation circuit (e.g., a venous system) via one or more inlets and/or a fresh media circuit (e.g., an arterial system) via one or more outlets.

In some embodiments, a computer can be used with the organ perfusion system to regulate variables such as temperature, air, $O_2$, $CO_2$, fluid flow rate, and perfusion pressure. The on-board computer also records culture variables (e.g., pH and $O_2$), and can be used to externally control the perfusion controller and/or the fluid management devices within the platform device and thereby can control fluid flow into and out of the platform device (and thereby the plurality of bio-assessment devices). In particular disclosed embodiments, the computer can be used to control valves of the fluid management devices to thereby control flow in and out of the channels of the of the fluid management devices (or integrated fluid management devices).

In some embodiments, the platform device can further comprise one or more microformulators. The microformulators can be used to prepare and facilitate precise delivery of desired amounts of perfusion media to the platform device. The microformulators can comprise a plurality of pneumatic microfluidic valves and solenoid valves to deliver perfusate to the bio-assessment devices from the organ perfusion system. In some embodiments, the microformulator is used to deliver nutrients, metabolites, hormones, paracrine signals, and/or drugs or agents to be analyzed using the platform device to one or more bio-assessment devices. In some embodiments, the microformulator is used to deliver nutrients, metabolites, hormones, paracrine signals, and/or drugs or agents being analyzed with the platform device that would be provided by organ devices not included for use in the platform (e.g., a device other than a heart device, lung device, kidney device, or liver device). In such embodiments, the microformulator can be referred to herein as a "missing organ" microformulator. Solely by way of example, a missing organ microformulator can be used in place of endocrine organs, the gut, and the brain and therefore can provide biological components, such as fatty acids and other biologically relevant molecular species. The microformulators can be used to provide controlled additions of nutrients, metabolites, hormones, paracrine signals, and/or drugs or agents to media passed through the platform device, the fluid management devices, and the bio-assessment devices (e.g., fluids, such as blood surrogate, air, and other biological media). A combination of microformulators for use with a bio-assessment device and missing organ microformulators can be used in the platform device. In some embodiments, an individual microformulator can be positioned upstream of each bio-assessment device to provide media supplements specifically required by a particular bio-assessment device. If specific molecules produced by or introduced into a particular bio-assessment device are toxic to another bio-assessment device, a size exclusion filter or an antibody-based affinity separator can be used in conjunction with the microformulator and the bio-assessment device to remove the toxic molecules from the perfusion stream that is fluidly coupled to that bio-assessment device. In particular disclosed embodiments, a microformulator can be used in combination with a countercurrent dialysis system to reduce the local concentration of specific molecules in media passing through the platform device and bio-assessment devices. Representative embodiments of a microformulator are described in U.S. Patent Application Publication No. 2014/0356849 and WO 2014/081840.

The platform devices disclosed herein can comprise one or more peristaltic pumps that are used to facilitate flow of media through the platform device and the various bio-assessment devices used with the platform. The pumps can be miniaturized, such as micropumps or nanopumps. The pumps are optionally used in combination with one or more of the microformulators. In some examples, the pumps are rotary peristaltic pumps such as those described in PCT Publication No. WO/2012/048261, which is incorporated herein by reference, as well as U.S. Patent Application Publication No. 2014/0356849. The peristaltic pumps can be used in combination with rotary planar valves, which also are described in PCT Publication No. WO/2012/048261 and U.S. Patent Application Publication No. 2014/0356849.

The platform devices disclosed herein also can comprise analyzers or sensors capable of detecting properties and the chemical make-up of fluids passed through the platform device, such as effluent exiting a bio-assessment device or perfusate entering a bio-assessment device. In some embodiments, the analyzers or sensors are integrated with the perfusion controller to form one singular component, and in other embodiments they are separate components. In some embodiments, the analyzers, sensors, and perfusion controllers can be used to prevent issues associated with calibration and fouling of in-line electrochemical sensors, to isolate the bio-assessment devices of the platform for seeding, diagnosis, and/or treatment protocols, for inter-bio-assessment device media balancing and shunting, and to provide additional local perfusion or gas exchange. In other examples, the analyzers or sensors are used to determine the functioning of one or more of the bio-assessment devices or the effect of one or more introduced compounds, for example on metabolism, secretion, gene expression, and so on. Analyzers can include one or more of devices or instrumentation for liquid chromatography (for example, high performance liquid chromatography or ultra performance liquid chromatography (UPLC)), mass spectrometry (MS; such as MS-MS, gas chromatography-MS, ion mobility-MS), or a combination thereof. In one example, the analyzer includes instrumentation for ultra performance liquid chromatography-ion mobility-MS.

In some embodiments of the disclosed platform devices, multichannel potentiostats can be used to measure dynamic changes in glucose, lactate, oxygen, and pH in cells and media used in the bio-assessment devices. Embodiments of a multichannel potentiostat that can be used with the disclosed platform devices are described, for example, in U.S. Patent Application Publication No. 2014/0356849.

V. Methods of Making Devices

In some embodiments, methods of making the fluid management devices disclosed herein comprise a layer-by-layer fabrication process by which patterned layers of films or sheet materials are produced and coupled to provide the substrates of the fluid management devices. In some embodiments, the layer-by-layer fabrication process includes patterning a network of channels into a substrate using a laser (e.g., laser ablation) to form channels in the substrate. In some embodiments, the layer-by-layer fabrication process can be performed manually or it can be automated. The channels formed during the layer-by-layer fabrication process can have any of the dimensions disclosed herein. The layer-by-layer fabrication process can be used to produce substrates comprising different channel configurations that, when the substrates are stacked vertically, will combine to form an integrated channel network through which fluids can flow between and through the stacked substrates. In some embodiments, the substrates can be physically combined by vertically stacking and then clamping the substrates together, or they can be stacked and adhered together, such as by using an adhesive and/or a lamination technique known to those of ordinary skill in the art.

Embodiments of the fluid management device can be made by making a connection substrate comprising one or more inlets, outlets, ports, or a combination thereof. A channel substrate also is made comprising at least one channel coupled to the inlets, outlets, ports, or a combination thereof. The inlets, outlets, and ports of the connection substrate can be formed using a laser, as can the channels of the channel substrate. Other means of forming inlets, outlets, ports, and channels are known to one of ordinary skill in the art, such as chemical etching, lithography (e.g., soft lithography), milling, three-dimensional printing or the like. In some embodiments, the fluid management device can be made using methods described by Nath et al. ("Rapid prototyping of robust and versatile microfluidic components using adhesive transfer tapes," *Lab Chip*, 2010, 10, 2286-2291, and/or "Polymerase chain reaction compatibility of adhesive transfer tape based microfluidic platforms," *J. Microsystem Tech.*, 20, 6, 2014, 1187-1193, the relevant portions of which are incorporated herein by reference). In particular disclosed embodiments, one or more tube lines can be attached, such as by using an adhesive, to the inlets and outlets of the connection substrate. The tube lines can be attached at any point of making the device. The connection substrate can be coupled with a channel substrate comprising one or more inlet, outlets, and/or channels that also can be made using a laser cutting technique. The inlets and/or outlets of the channel substrate can be aligned with the inlets and outlets of the connection substrate so that one or more fluids can flow there through. The connection substrate and the channel substrate can be coupled using a suitable adhesive or adhesive tape (single-sided and/or double-sided) known to those of ordinary skill in the art, or they can be laminated together.

VI. Methods of Using Devices

The devices disclosed herein can be used to facilitate fluid delivery in a devices used for chemical and/or biological processes. In one non-limiting example, the devices are used to facilitate fluid delivery in bio-assessment devices used to mimic organs. In particular disclosed embodiments, the fluid management devices disclosed herein are single or multi-layered planar channel devices that can replace tubing-based flow networks used with reactors, such as bio-assessment devices. The devices disclosed herein can be used to manually operate embodiments of reactors, or they can be automated.

In some embodiments, the devices disclosed herein can be used in chemical synthesis to facilitate delivery of solvents and reagents to and from reactors during synthesis. For example, the fluid management device can be connected to one or more reservoirs as described herein. The reservoir can comprise one or more chambers that house solvents, chemical reagents, and combinations thereof. A pump or other suitable delivery device is connected to the reservoir via the fluid management device. The pump or delivery device is switched on so as to draw the solvents, chemical reagents, or combinations thereof from the reservoir through channels of the channel network of the fluid management device. The valving system is manipulated to control when and how much of the solvents, chemical reagents, or combinations thereof are delivered into a reaction vessel that is fluidly coupled to the fluid management system. Pinch valves, latching solenoid valves, or combinations thereof can be used in combination with the arch valves attached to the fluid management system to manually control fluid flow or such valves can be automated and controlled via a computer.

In some other embodiments, the devices disclosed herein can be used in combination with bio-assessment devices, such as bio-assessment devices used to mimic animal organ function. Exemplary such bio-assessment devices are described in International Patent Application No. PCT/US2015/052039, entitled "BIO-ASSESSMENT DEVICE AND METHOD OF MAKING THE DEVICE,", filed on Sep. 24, 2015. In such embodiments, the devices can be used to facilitate delivery of fluids (e.g., air, liquids, biological media, and the like) into and out of the bio-assessment device(s). The devices also can be used to deliver reagents (e.g., chemicals, drugs, etc.) into the bio-assessment device for analysis. In exemplary embodiments, the devices disclosed herein can be used for flow based sterilization, washing, priming bio-assessment devices with media, cell seeding, drug introduction, sample collection, media exchange, waste withdrawal, and combinations thereof. In yet additional embodiments, the fluid management devices and other components disclosed herein can be used to facilitate communication (e.g., fluid communication) between a variety of bio-assessment devices.

In view of the many possible embodiments to which the principles of the present disclosure may be applied, it should be recognized that the illustrated embodiments are only examples and should not be taken as limiting the scope of the claimed invention. Rather, the scope of the disclosure is defined by the following claims. We therefore claim all that comes within the scope and spirit of these claims.

We claim:

1. An integrated device, comprising:
   a fluid management device including:
      a unitary channel substrate made of a biocompatible and/or polymeric material comprising a first surface and a second surface and one or more channels defined in the first surface of the unitary channel substrate;
      a unitary connection substrate made of a biocompatible and/or polymeric material comprising an external surface and second surface and one or more inlets and/or outlets and wherein the unitary channel substrate is stacked vertically with the unitary connection substrate such that the first surface of the unitary channel substrate touches the second surface of the unitary connection substrate and such that the one or more channels of the unitary channel substrate are fluidly aligned with the one or more inlets and/or outlets of the unitary connection substrate; and
      a valving system comprising a flexible tube configured to deliver fluid through an interior of the flexible tube to the one or more channels of the unitary channel substrate, wherein the flexible tube forms an arch configuration that extends off-plane from the external surface of the unitary connection substrate and wherein both ends of the flexible tube are coupled to the external surface of the unitary connection substrate; and
   a reservoir including:
      one or more chambers for housing a fluid;
      one or more integrated flow channels located along one or more walls of the one or more chambers; and
      one or more ports for delivering fluid to or from the one or more chambers.

2. The integrated device of claim 1, further comprising one or more reactors fluidly coupled to the integrated device.

3. The integrated device of claim 1, wherein the one or more reactors is a bio-assessment device.

4. The integrated device of claim 3, wherein the one or more bio-assessment devices is a lung organ device, a heart device, a liver device, a kidney device, a gastrointestinal device, a vascular device, a neuronal device, or a combination of two or more.

5. The integrated device of claim 3, wherein the integrated device is fluidly coupled to (i) an organ perfusion system in fluid communication with a fresh media circuit and a recirculation circuit, wherein the fresh media circuit is coupled to an inlet of the bio-assessment device through the fluid management device and the recirculation circuit is fluidly coupled to an outlet of the bio-assessment device through the fluid management device; (ii) one or more rotary peristaltic pumps capable of pumping fluid to one or more rotary planar valves; and/or (iii) a perfusion controller coupled to the organ perfusion system.

6. The integrated device of claim 5, further comprising an analyzer, a sensor, or a combination thereof coupled to the perfusion controller.

7. The integrated device of claim 5, further comprising one or more microformulators fluidly coupled to the fresh media circuit and the recirculation circuit.

8. The integrated device of claim 1, further comprising one or more pumps physically coupled to the integrated device.

9. The integrated device of claim 1, wherein the one or more channels are microchannels, nanochannels, or large-sized channels.

10. The integrated device of claim 1, wherein the one or more chambers comprise a readable scale for visually determining the amount of fluid in the chambers.

11. The integrated device of claim 1, wherein the integrated flow channels are formed within the one or more chambers.

12. The integrated device of claim 1, further comprising one or more additional unitary channel substrates fluidly coupled with and positioned adjacent to the second surface of the unitary channel substrate.

13. The integrated device of claim 1, further comprising one or more valves capable of deforming the flexible tube to restrict fluid flow through the flexible tube.

14. The integrated device of claim 13, wherein the one or more valves are selected from pinch valves, latching solenoid valves, or combinations thereof.

* * * * *